United States Patent
Bark et al.

(10) Patent No.: US 9,452,152 B2
(45) Date of Patent: Sep. 27, 2016

(54) FE(III) COMPLEX COMPOUNDS FOR THE TREATMENT AND PROPHYLAXIS OF IRON DEFICIENCY SYMPTOMS AND IRON DEFICIENCY ANEMIAS

(71) Applicant: Vifor (International) AG, St. Gallen (CH)

(72) Inventors: Thomas Bark, Zürich (CH); Wilm Buhr, Constance (DE); Susanna Burckhardt, Zürich (CH); Michael Burgert, Friedrichshafen (DE); Camillo Canclini, St. Gallen (CH); Franz Dürrenberger, Dornach (CH); Felix Funk, Winterthur (CH); Peter O. Geisser, St. Gallen (CH); Aris Kalogerakis, Winterthur (CH); Simona Mayer, Bühler (CH); Erik Philipp, Arbon (CH); Stefan Reim, Stadel Winterthur (CH); Diana Sieber, Abtwil (CH); Jörg Schmitt, Gaienhofen (DE); Katrin Schwarz, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 0 days.

(21) Appl. No.: 14/650,325

(22) PCT Filed: Dec. 19, 2013

(86) PCT No.: PCT/EP2013/077383
§ 371 (c)(1),
(2) Date: Jun. 8, 2015

(87) PCT Pub. No.: WO2014/096193
PCT Pub. Date: Jun. 26, 2014

(65) Prior Publication Data
US 2015/0313864 A1 Nov. 5, 2015

(30) Foreign Application Priority Data

Dec. 21, 2012 (EP) .................................. 12199075

(51) Int. Cl.
A61K 31/295 (2006.01)
A61K 31/555 (2006.01)
A61K 45/06 (2006.01)

(52) U.S. Cl.
CPC ........... *A61K 31/295* (2013.01); *A61K 31/555* (2013.01); *A61K 45/06* (2013.01)

(58) Field of Classification Search
None
See application file for complete search history.

(56) References Cited

U.S. PATENT DOCUMENTS

2013/0109662 A1  5/2013  Bark et al.

FOREIGN PATENT DOCUMENTS

| CH | WO 2011117225 A1 * | 9/2011 | ........... A61K 31/295 |
| WO | 2012/163938 A1 | 12/2012 | |

OTHER PUBLICATIONS

International Search Report for corresponding PCT/EP2013/077383 mailed Feb. 17, 2014, three pages.
Banville et al., "(Z)-2,2-Dimethyl-5-carboxymethylene-1,3-dioxolan-4-one: a new synthon for the synthesis of alpha, gamma-diketoacid derivatives," Tetrahedron Letters 51 (2010) pp. 3170-3173.
Thomas-Mamert, "Organic Chemistry," Bullletin de la Societe Chimique de Paris, 1894, pp. 96-98.
Translation of Thomas-Mamert, "Organic Chemistry," Bullletin de la Societe Chimique de Paris, 1894, three pages.
International Preliminary Report on Patentability for corresponding PCT/EP2013/077383 mailed Jul. 2, 2015, 15 pages.

* cited by examiner

*Primary Examiner* — Nyeemah A Grazier
(74) *Attorney, Agent, or Firm* — Rankin, Hill & Clark LLP

(57) ABSTRACT

The invention relates to iron(III) complex compounds and pharmaceutical compositions comprising them for the use as medicaments, in particular for the treatment and/or prophylaxis of iron deficiency symptoms and iron deficiency anemias.

18 Claims, No Drawings

FE(III) COMPLEX COMPOUNDS FOR THE TREATMENT AND PROPHYLAXIS OF IRON DEFICIENCY SYMPTOMS AND IRON DEFICIENCY ANEMIAS

INTRODUCTION

The invention relates to iron(III)-2-oxo-butanediamide complex compounds and pharmaceutical compositions comprising them for the use as medicaments, in particular for the treatment and/or prophylaxis of iron deficiency symptoms and iron deficiency anemias.

BACKGROUND

Iron is an essential trace element for almost all organisms and is relevant in particular with respect to growth and the formation of blood. The balance of the iron metabolism is in this case primarily regulated on the level of iron recovery from haemoglobin of ageing erythrocytes and the duodenal absorption of dietary iron. The released iron is taken up via the intestine, in particular via specific transport systems (DMT-1, ferroportin, transferrin, transferrin receptors), transferred into the blood circulation and thereby conveyed to the appropriate tissues and organs.

In the human body, the element iron is of great importance for oxygen transport, oxygen uptake, cell functions such as mitochondrial electron transport, and ultimately for the entire energy metabolism.

On average, the human body contains 4 to 5 g iron, with it being present in enzymes, in haemoglobin and myoglobin, as well as depot or reserve iron in the form of ferritin and hemosiderin.

Approximately half of this iron, about 2 g, is present as heme iron, bound in the haemoglobin of the erythrocytes. Since these erythrocytes have only a limited lifespan (75-150 days), new ones have to be formed constantly and old ones eliminated (over 2 million erythrocytes are being formed per second). This high regenerative capacity is achieved by macrophages phagocytizing the ageing erythrocytes, lysing them and thus recycling the iron thus obtained for the iron metabolism. The amount of iron of about 25 mg required daily for erythropoiesis is thus provided for the main part.

The daily iron requirement of an adult human is between 0.5 to 1.5 mg per day, infants and women during pregnancy require 2 to 5 mg of iron per day. The daily iron loss, e.g. by desquamation of skin and epithelial cells, is low; increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake. The iron level is regulated by absorption, with the absorption rate of the iron present in food being between 6 and 12%; in the case of iron deficiency, the absorption rate is up to 25%. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or discharged into the blood by the transport protein ferroportin. Hepcidin plays a central role in this process because it is the most important regulating factor of iron uptake. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, Cell 117, 2004, 285-297.)

Mammalian organisms are unable to actively discharge iron. The iron metabolism is substantially controlled by hepcidin via the cellular release of iron from macrophages, hepatocytes and enterocytes.

In pathological cases, a reduced serum iron level leads to a reduced hemoglobin level, reduced erythrocyte production and thus to anemia.

External symptoms of anemias include fatigue, pallor as well as reduced capacity for concentration. The clinical symptoms of an anemia include low serum iron levels (hypoferremia), low hemoglobin levels, low hematocrit levels as well as a reduced number of erythrocytes, reduced reticulocytes and elevated levels of soluble transferrin receptors.

Iron deficiency symptoms or iron anemias are treated by supplying iron. In this case, iron substitution takes place either orally or by intravenous iron administration. Furthermore, in order to boost erythrocyte formation, erythropoietin and other erythropoiesis-stimulating substances can also be used in the treatment of anemias.

Anemia can often be traced back to malnutrition or low-iron diets or imbalanced nutritional habits low in iron. Moreover, anemias occur due to reduced or poor iron absorption, for example because of gastroectomies or diseases such as Crohn's disease. Moreover, iron deficiency can occur as a consequence of increased blood loss, such as because of an injury, strong menstrual bleeding or blood donation. Furthermore, an increased iron requirement in the growth phase of adolescents and children as well as in pregnant women is known. Since iron deficiency not only leads to a reduced erythrocyte formation, but thereby also to a poor oxygen supply of the organism, which can lead to the above-mentioned symptoms such as fatigue, pallor, reduced powers of concentration, and especially in adolescents, to long-term negative effects on cognitive development, a highly effective and well tolerated therapy is of particular interest.

Through using the Fe(III) complex compounds according to the invention, there is the possibility of treating iron deficiency symptoms and iron deficiency anemias effectively by oral application without having to accept the large potential for side effects of the classical preparations, the Fe(II) iron salts, such as $FeSO_4$, which is caused by oxidative stress. Poor compliance, which often is the reason for the deficient elimination of the iron deficiency condition, is thus avoided.

PRIOR ART

A multitude of iron complexes for the treatment of iron deficiency conditions is known from the prior art.

A very large proportion of these complex compounds consists of polymer structures. Most of these complex compounds are iron-polysaccharide complex compounds (WO20081455586, WO2007062546, WO20040437865, US2003236224, EP150085). It is precisely from this area that there are medicaments available on the market (such as Maltofer, Venofer, Ferinject, Dexferrum, Ferumoxytol).

Another large portion of the group of the polymer complex compounds is comprised of the iron-peptide complex compounds (CN101481404, EP939083, JP02083400).

There are also Fe complex compounds described in the literature that are structurally derived from macromolecules such as hemoglobin, chlorophyll, curcumin and heparin (U.S. Pat. No.474670, CN1687089, Biometals, 2009, 22, 701-710).

Moreover, low-molecular Fe complex compounds are also described in the literature. A large number of these Fe complex compounds comprises carboxylic acid and amino acids as ligands. In this case, the focus is on aspartate (US2009035385) and citrate (EP308362) as ligands. Fe complex compounds containing derivatized phenylalanine groups as ligands are also described in this context (ES2044777).

Further, Fe-complex compounds are described in the literature, which are built from monomeric sugar units or of a combination of monomeric and polymeric units (FR19671016).

US 2005/0192315 discloses pharmaceutical compositions containing quinoline compounds which formally contain a 2-(hydroxymethylene)-propanediamide, thus a propanediamide structural element. Accordingly, they do not contain a 2-oxo-butanediamide structural element.

Hydroxypyrone and hydroxypyridone Fe complex compounds are also described in the literature (EP159194, EP138420, EP107458). The corresponding 5-ring systems, the hydroxyfuranone Fe complex compounds, are also described in analogy thereto (WO2006037449).

In addition, also Fe complex compounds with pyrimidine-2-ol-1-oxide ligands are described in the literature that should be used for the treatment of iron deficiency anemia (WO2012130882). The WO2012163938 describes iron (III) -2,4-dioxo-1-carbonyl complex compounds, which shall also be used for the treatment of iron deficiency anemia.

Furthermore, Fe complexes with β-keto amide ligands are described in the literature, their use being proposed for the treatment of iron deficiency conditions (WO2011117225). An indication of Fe(III) complex compounds with 2-oxo-butanediamide ligand cannot be found in this application. Furthermore, the Fe complexes with β-keto amide ligands are in particular with regard to their water solubility and their iron utilization in need of improvement.

Iron salts (e.g. iron(II) sulfate, iron(II) fumarate, iron(III) chloride, iron(II) aspartate, iron(II) succinate) are another important constituent for the treatment of iron deficiency symptoms and iron deficiency anemias.

These iron salts are very problematic in that, in part, they are highly incompatible (up to 50%) in the form of nausea, vomiting, diarrhea and also obstipation and cramps. Moreover, free iron(II) ions which catalyze the formation (inter alia Fenton reaction) of reactive oxygen species (ROS) occur during the use of these iron(II) salts. These ROS cause damage to DNA, lipids, proteins and carbohydrates which has far-reaching effects in cells, tissue and organs. This complex of problems is known and, in the literature, is largely considered the cause for the high incompatibility and referred to as oxidative stress.

OBJECT:

The object of the present invention lay in developing new therapeutically effective compounds with good activity, iron utilisation, complex stability and solubility, respectively, particularly good stability and good solubility in the pH of neutral aqueous media, that can be used for an effective therapy for the oral treatment of iron deficiency symptoms and iron deficiency anemias. Particularly a good stability and a good solubility is very important for an effective oral iron therapy.

Further, these iron complexes were supposed to exhibit significantly fewer side effects or a lower toxicity, particularly in comparison to the classically used Fe(II) salts. Furthermore, these iron complexes, in contrast to the known polymeric iron complex compounds, were supposed to have a defined structure (stoichiometry) and to be preparable by simple synthesis processes. This goal was achieved by the development of novel Fe(III) complex compounds.

Furthermore, the novel iron complexes were supposed to be designed such that they are taken up into the intestinal cells directly via the membrane in order thus to release their complex-bound iron directly to the ferritin or the transferrin or to reach the bloodstream directly as an intact complex. Because of their properties, these new complexes are supposed to virtually not lead to the occurrence of high concentrations of free iron ions. For it is precisely the free iron ions that lead to the occurrence of ROS which are ultimately responsible for the side effects that occur.

In order to be able to meet these requirements, the inventors developed new Fe(III) complex compounds with a molecular weight that is not too large, medium lipophilicity, very good activity or iron utilisation, respectively, high water solubility and an optimal pH-dependent complex stability.

In the development of the new complexes, the stability improvement particularly in neutral aqueous media should not be achieved at the expense of solubility, since for oral use the solubility is a very important criterion. This combined goal is achieved by the Fe complexes of the invention. They show a good stability in aqueous medium at neutral pH, and at the same time have a very good solubility in water. Thus the iron complex compounds of the invention allow to achieve a much faster treatment success.

DESCRIPTION OF THE INVENTION

The inventors surprisingly found that novel Fe(III) complex compounds with 2-oxo-butanediamide ligands were particularly suitable for the above-described requirements. It was possible to demonstrate that these Fe complex compounds exhibited a high iron uptake, whereby a quick therapeutic success in the treatment of iron deficiency anemia could be achieved. Especially in comparison to iron salts, the complex compounds according to the invention exhibited a faster and higher utilization. Furthermore, these new systems have significantly reduced side effects than the classically used iron salts since there is no noteworthy occurrence of free iron irons in this case. The complex compounds according to the invention exhibit almost no oxidative stress since there is no formation of free radicals. Thus, significantly fewer side effects occur in the case of these complex compounds than in the case of the Fe salts known from the prior art. The complex compounds exhibit good stability at acidic as well as at neutral pH value ranges, which is particularly advantageous for oral applications. The complex compounds can be prepared well and are optimally suitable for the formulation of medicaments, in particular for oral administration.

Thus, the subject matter of the invention are iron(III)-2-oxo-butanediamide complex compounds or their salts, particularly pharmaceutically acceptable salts for use as medicaments. The subject matter of the invention are thus also iron(III)-2-oxo-butanediamide complex compounds or their pharmaceutically acceptable salts for use in a method for therapeutic treatment of the human or animal body, respectively.

The iron(III)-2-oxo-butanediamide complex compounds as used in accordance with the present invention particularly include such compounds which comprise at least one ligand of the formula (I):

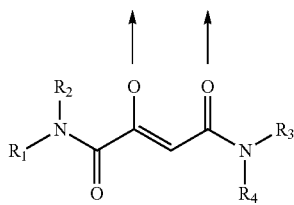

(I)

wherein
the arrows respectively represent a coordinate bond to an iron atom,
$R_1$ and $R_2$ are the same or different and are respectively selected from the group consisting of hydrogen and optionally substituted alkyl,
or
$R_1$ and $R_2$ together with the nitrogen atom, to which they are bonded, form an optionally substituted 3- to 6-membered ring, which may optionally contain one further heteroatom,
$R_3$ and $R_4$ are the same or different and are respectively selected from the group consisting of hydrogen and optionally substituted alkyl, or
$R_3$ and $R_4$ together with the nitrogen atom, to which they are bonded, form an optionally substituted 3- to 6-membered ring, which may optionally contain one further heteroatom, or pharmaceutically acceptable salts thereof.

Preferred are in particular iron(III)-2-oxo-butanediamide complex compounds which comprise at least one ligand of the formula (I):

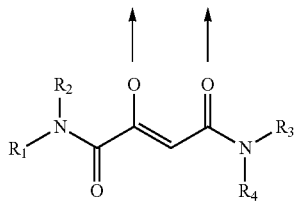

(I)

wherein
the arrows respectively represent a coordinate bond to one or different iron atoms,
$R_1$ and $R_2$ are the same or different and are respectively selected from the group consisting of hydrogen, methyl, ethyl, propyl, isopropyl, n-butyl, sek-butyl and tert-butyl, and wherein said alkyl groups may be substituted with a substituent which is selected from the group consisting of: alkoxy, alkoxycarbonyl, aminocarbonyl ($H_2NCO$—), monoalkylaminocarbonyl and dialkylaminocarbonyl, or
$R_1$ and $R_2$ together with the nitrogen atom, to which they are bonded, form an optionally substituted 5- to 6-membered ring, which may optionally contain one further heteroatom, $R_3$ and $R_4$ are the same or different and are respectively selected from the group consisting of hydrogen and optionally substituted alkyl, and optionally substituted cycloalkyl, wherein in said alkyl groups optionally one or two carbon atoms may be replaced by oxygen, or
$R_3$ and $R_4$ together with the nitrogen atom, to which they are bonded, form an optionally substituted 3- to 6-membered ring, which may optionally contain one further heteroatom.

Further preferred are in particular iron(III)-2-oxo-butanediamide complex compounds which comprise at least one ligand of the formula (I):

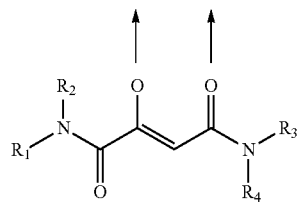

(I)

wherein
the arrows respectively represent a coordinate bond to one or different iron atoms,
$R_1$ and $R_2$ are the same or different and are respectively selected from the group consisting of hydrogen, methyl, ethyl, propyl, i-propyl, n-butyl, sek-butyl and Cert-butyl, and wherein the alkyl groups may be substituted with a substituent which is selected from the group consisting of: alkoxy, alkoxycarbonyl, aminocarbonyl ($H_2NCO$—), monoalkylaminocarbonyl and dialkylaminocarbonyl, or
$R_1$ and $R_2$ together with the nitrogen atom, to which they are bonded, form pyrrolidinyl,
$R_3$ and $R_4$ are the same or different and are respectively selected from the group consisting of hydrogen, alkyl and cycloalkyl, wherein alkyl and cycloalkyl may optionally be substituted with a substituent which is selected from the group consisting of hydroxyl, alkoxy, alkoxycarbonyl, aminocarbonyl ($H_2NCO$—), monoalkylaminocarbonyl and dialkylaminocarbonyl,
$R_3$ and $R_4$ together with the nitrogen atom, to which they are bonded, form morpholinyl or pyrrolidinyl, wherein said ring groups may be substituted with hydroxyl.

Particularly preferred are further iron(III)-2-oxo-butanediamide complex compounds which comprise at least one ligand of the formula (I):

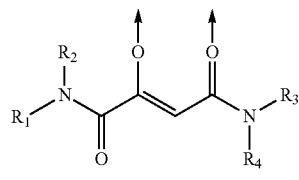

(I)

wherein
the arrows respectively represent a coordinate bond to one or different iron atoms,
$R_1$ and $R_2$ are the same or different and are respectively selected from the group consisting of hydrogen, methyl, ethyl, propyl, isopropyl, n-butyl, sek-butyl and isobutyl, $R_3$ and $R_4$ are the same or different and are respectively selected from the group consisting of hydrogen and optionally substituted alkyl, or $R_3$ and $R_4$ together with the nitrogen atom, to which they are bonded, form an optionally substituted 3- to 6-membered ring, which may optionally contain one further heteroatom.

Particularly preferred iron(III) complex compounds comprise at least one ligand of the formula (I):

(I)

wherein the arrows respectively represent a coordinate bond to one or different iron atoms, $R_1$ and $R_2$ are the same or different and are respectively selected from the group consisting of hydrogen and methyl, $R_3$ and $R_4$ are the same or different and are respectively selected from the group consisting of hydrogen and optionally substituted alkyl.

Particularly preferred are iron(III) complex compounds of the formula (II):

(II)

wherein $R_1$, $R_2$, $R_3$ and $R_4$ are as defined above.

Preferably, the molecular weight of the iron(III)-2-oxobutanediamide complex compounds according to the invention is less than 1000 g/mol, more preferably less than 800 g/mol (in each case determined from the structural formula).

Within the overall context of the invention, optionally substituted alkyl, in particular for the substituents $R_1$ to $R_4$, preferably includes: straight-chained or branched alkyl with 1 to 6 carbon atoms, cycloalkyl with 3 to 6, preferably 5 or 6 carbon atoms, or alkyl with 1 to 4 carbon atoms, which is substituted with cycloalkyl, wherein these alkyl groups each can be optionally substituted.

The above mentioned alkyl groups can optionally each preferably be substituted with 1 to 3 substituents. More preferably they are not substituted.

The substituents of alkyl are preferably selected from the group consisting of: hydroxy, alkoxy, alkoxycarbonyl, aminocarbonyl, ($H_2NCO$—), monoalkylaminocarbonyl and dialkylaminocarbonyl, especially as defined below. With respect to the alkyl groups in said substituent groups alkoxy, alkoxycarbonyl, monoalkylaminocarbonyl and dialkylaminocarbonyl reference can be made to the above and the following definition of alkyl.

The substituents of alkyl are preferably selected from the group consisting of: hydroxyl and optionally substituted alkoxy, in particular as defined below.

In the above defined alkyl groups, optionally one or more carbon atoms can furthermore be replaced by oxygen. This means, in particular, that one or more methylene group (—$CH_2$—) can be replaced in the alkyl groups by —O—.

Examples of alkyl residues having 1 to 6 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, etc. Those with 1 to 4 carbon atoms are preferred. Methyl, ethyl, n-propyl and n-butyl are most preferred.

Cycloalkyl groups with 3 to 6 carbon atoms preferably include: a cyclopropyl group, a cyclobutyl group, a cyclopentyl group, and a cyclohexyl group. The cycloalkyl residues may optionally be substituted preferably by one substituent such as hydroxyl, methyl or methoxy.

The definition of the optionally substituted alkyl groups also includes alkyl groups which are substituted by the above mentioned cycloalkyl groups, such as cyclopropylmethyl, cyclobutylmethyl, cyclopentylmethyl or cyclohexylmethyl.

Examples of an alkyl residue substituted with hydroxy include the above-mentioned alkyl residues, which have 1 to 2 hydroxy residues, such as, for example hydroxymethyl, 2-hydroxyethyl, 3-hydroxypropyl, 4-hydroxybutyl, etc.

Optionally substituted alkoxy (RO—) includes in context with the present invention, for example, linear or branched alkoxy residues, preferably with up to 4 carbon atoms, such as a methoxy group, an ethoxy group, an n-propyloxy group, and an i-propyloxy group. The alkoxy groups may optionally be substituted, such as for example with the above possible substituents for alkyl, particularly with 1 to 3, preferably 1 substituent.

Methoxy and ethoxy are preferred alkoxy.

Alkoxycarbonyl includes in context with the present invention the aforementioned alkoxy, to which a carbonyl group is bonded (schematically: RO(C=O)—, wherein R is alkyl as mentioned before). Examples include methoxycarbonyl and ethoxycarbonyl.

Monoalkylaminocarbonyl and dialkylaminocarbonyl include in context with the present invention schematically residues of the formulas HRN—C(=O)— and $R_2$N—C(=O)—, wherein with respect to the alkyl groups (R) reference is made to the aforementioned definition of alkyl. Examples include: methylaminocarbonyl and dimethylaminocarbonyl.

According to the invention the 2-oxo-butanediamide complex ligand includes the respective basic structure:

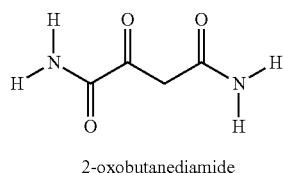

2-oxobutanediamide as well as all compounds, wherein one or more of the present hydrogen atoms are substituted by other atoms or atom groups, respectively, wherein for the formation of the subsequently described keto-enol-tautomerism at least one hydrogen atom must be present between the two coordinating C=O groups.

It is clear to the person skilled in the art that the 2-oxo-butanediamide complex ligands according to the invention, particularly the ligands of the formula (I)

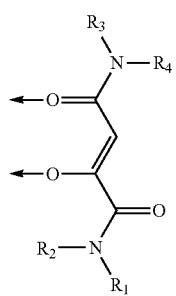

(I)

arise from the corresponding 2-oxo-butanediamide compounds (III):

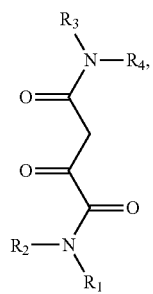

(III)

in which there is a keto-enol tautomerism, as is known:

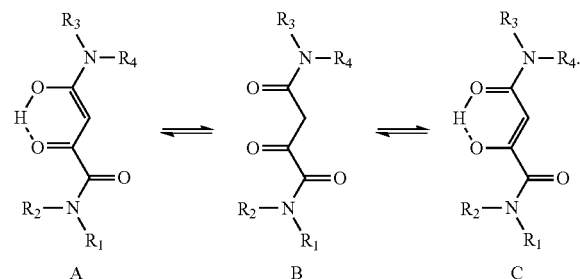

A    B    C

The mesomeric forms A and C are analytically indistinguishable. In the context of the present invention in each case, all forms are included, but in the context of the present invention the ligand in general, is only drawn in the keto form.

Formally, the ligand formally arises from the corresponding enol form A or C by abstraction of a proton:

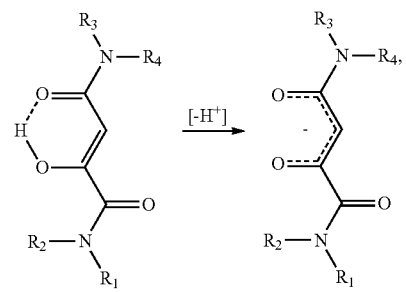

formally therefore carries a uninegative charge. Also for the iron complex compounds in the context of the present invention always only one of the localized resonance formulas is depicted:

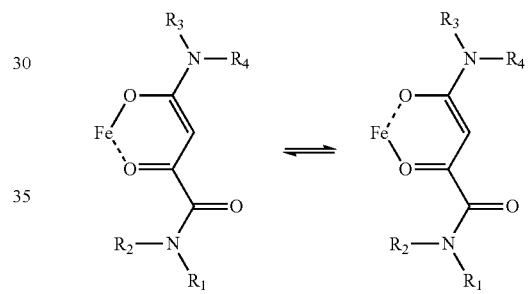

A    C although due to the lower electron density at the amidic oxygen atom of the amide group in the 1,3 position relative to the keto group, it is to be expected that the resonance formula C prevails. As explained above, an analytical distinction of the resonance formulas A and C is not possible. The other amide group, which is in the 1,2 position relative to the keto group, due to the analytical data does not appear to be involved in iron binding mode. IR measurements on the complex were able to show that only a very small shift of the IR bands between free ligand and complex could be observed for this amide group, which argues against a binding participation of this carbonyl group on the iron complex.

Examples of 2-oxo-butanediamide ligands used in accordance with the present invention are shown below:

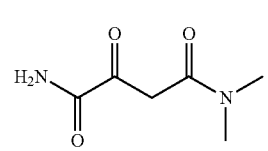

The invention further relates to a method for the preparation of the iron(III) complex compounds according to the invention which comprises the reaction of a 2-oxo-butanediamide (III) with an iron(III) salt (IV).

2-Oxo-butanediamides include in particular those of the formula (III):

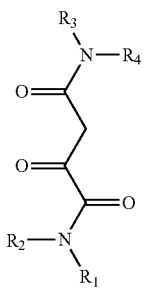

(III)

wherein $R_1$ to $R_4$ are defined as above.

Examples of suitable iron(III) salts include: iron(III) chloride, iron(III) acetate, iron(III) sulfate, iron(III) nitrate and iron(III) acetylacetonate, among which iron(III) chloride is preferred.

A preferred method is shown in the following scheme:

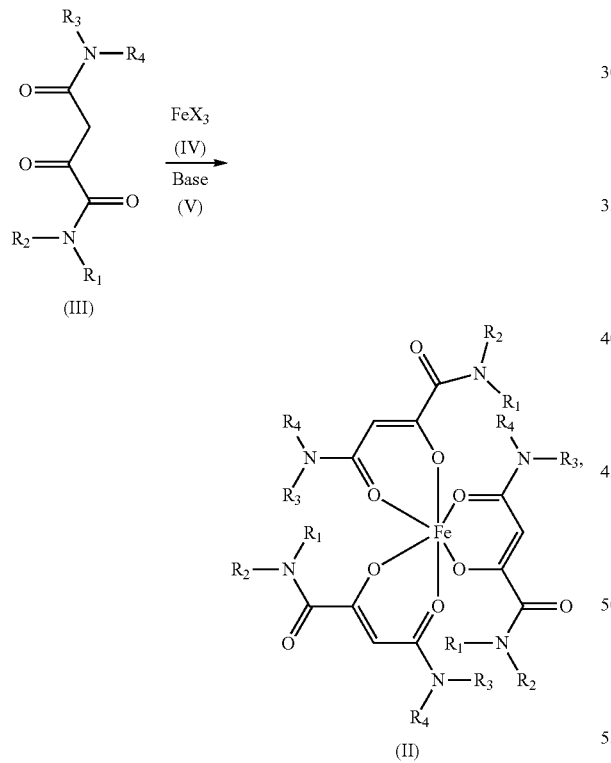

wherein $R_1$ to $R_4$ are as defined above, X is an anion such as halogenide, such as chloride, a carboxylate, such as acetate, sulphate, nitrate and acetylacetonate and base is a common organic or inorganic base.

In the method according to the invention, preferably 3-5 eq ligand (III), using suitable iron(III) salts (IV) (in this case Fe(III) chloride, Fe(III) acetate, Fe(III) sulphate and Fe(III) acetylacetonate are particularly suitable), are reacted under standard conditions to form the corresponding complexes of the general formula (II). In this case, the synthesis is carried out under the pH conditions optimal for complex formation. The optimum pH value is optionally set by adding a base (V), in this case, the use of sodium acetate, triethylamine, sodium carbonate, sodium hydrogen carbonate, sodium methanolate, sodium ethanolate, potassium carbonate, potassium hydrogen carbonate or potassium methanolate is particularly suitable.

The ligands (III) required for the preparation of the complexes are either commercially available or where prepared according to the following synthesis method. For this purpose, the following synthesis route was used.

In the case of partially substituted amides (III) (($R_1$=H; $R_2$=H or $R_2 \neq$H; $R_3$,$R_4 \neq$H) initially ester 6 is prepared from an oxalic acid ester of the general formula 4 and a dialkylacetamide of the general formula 5 by basic condensation reaction. (R. J. Gobeil et al, *Journal of the American Chemical Society*, 1945, 67, 511). As the bases various condensation bases, such as for example butyllithium, lithium diisopropylamine, sodium, sodium hydride, sodium amide, sodium alkoxides, potassium, potassium hydride, potassium amide and potassium alkoxides are suitable, with potassium tert-butoxide being preferred.

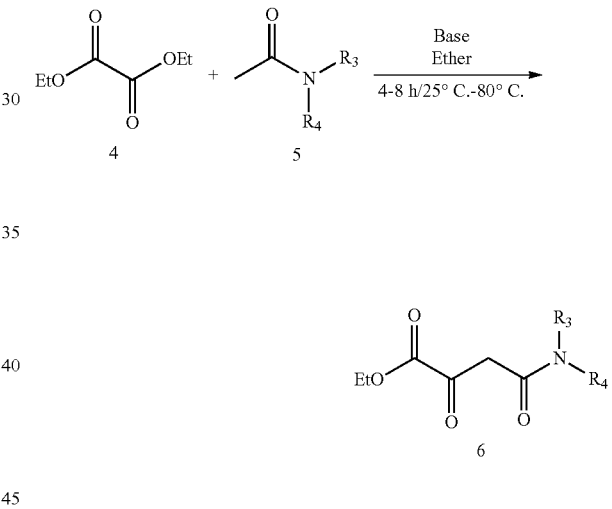

For the preparation of amide (III) ester 6 is converted into a metal complex 7. The preferred metal is copper, although other transition metals are suitable, too. Subsequently, the metal complex 7 is reacted with the respective amine to a metal complex of amide (III). Amide (III) is subsequently released from the corresponding metal complex with dilute mineral acid (A. Ichiba et al, *Journal of the Scientific Research Institute, Tokyo*, 1948, 23, 23-29), whereby in the case of copper, dilute sulfuric acid is preferred. In case that the amide (III) is too water soluble, the release can also be effected with hydrogen sulfide in an organic solvent, wherein methanol is preferred.

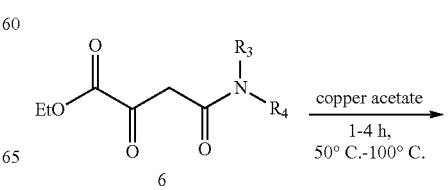

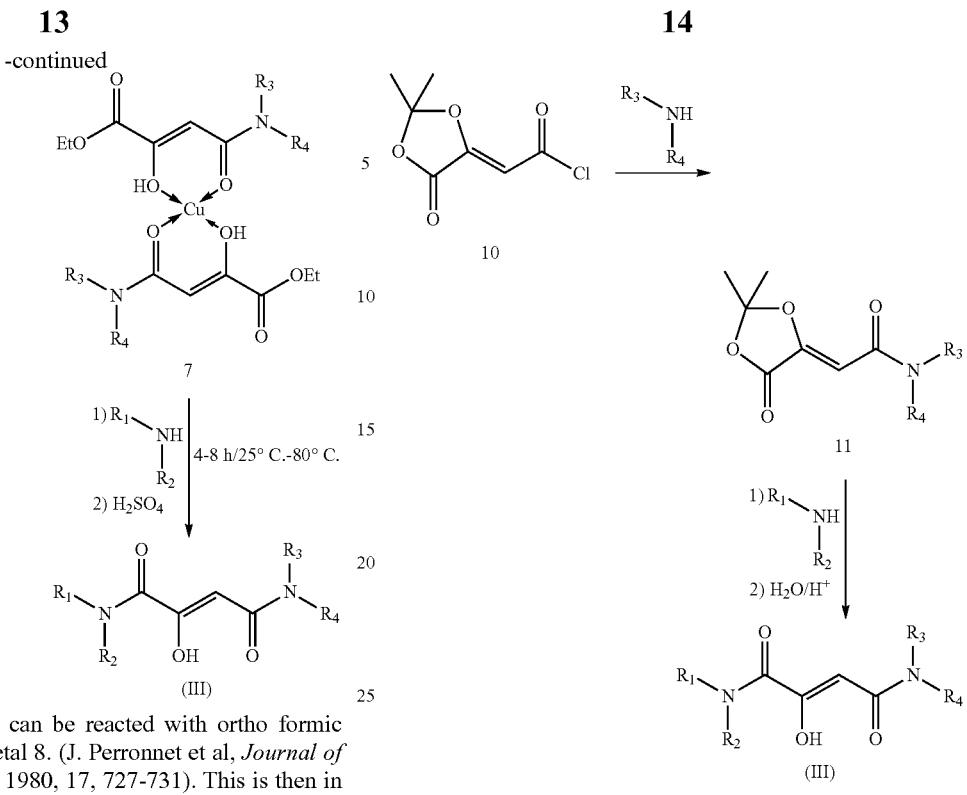

Alternatively, ester 6 can be reacted with ortho formic acid alkyl ester to the ketal 8. (J. Perronnet et al, *Journal of Heterocyclic Chemistry*, 1980, 17, 727-731). This is then in each case reacted with the respective amines to the corresponding diamide complex, which is hydrolyzed to amide (III) in aqueous acidic processing. (W. Kantlehner et al, *Liebigs Annalen der Chemie*, 1980, 9, 1448-1454).

As another method for the preparation of amide (III) with any substitution ($R_1$=H or $R_1$≠H; $R_2$=H or $R_2$≠H; $R_3$=H or $R_3$≠H, $R_4$=H or $R_4$≠H) the synthesis is carried out starting from (2Z)-(2,2-dimethyl-5-oxo-1,3-dioxolane-4-yliden) acetyl chloride. Here, the acid chloride 10 is reacted with the respective amine to acetonide 11, which is opened to the amide (III) in a second reaction step. (J. Banville et al, *Tetrahedron Letters*, 2010, 51, 3170-3173).

To achieve an improvement in yield in the final step, the acetonide 11, can initially be reacted with a metal complex 7a (with $R_3$=H, or $R_3$≠H, $R_4$=H, or $R_4$≠H). The preferred metal is copper, although other transition metals are suitable, too. Subsequently, the metal complex 7a is reacted with the respective amine to a metal complex of the amide (III). Amide (III) is subsequently released from the corresponding metal complex with dilute mineral acid (A. Ichiba et al, *Journal of the Scientific Research Institute, Tokyo*, 1948, 23, 23-29), whereby in the case of copper, dilute sulfuric acid is preferred. In case that the amide (III) is too water soluble, the release can also be effected with hydrogen sulfide in an organic solvent, wherein methanol is preferred.

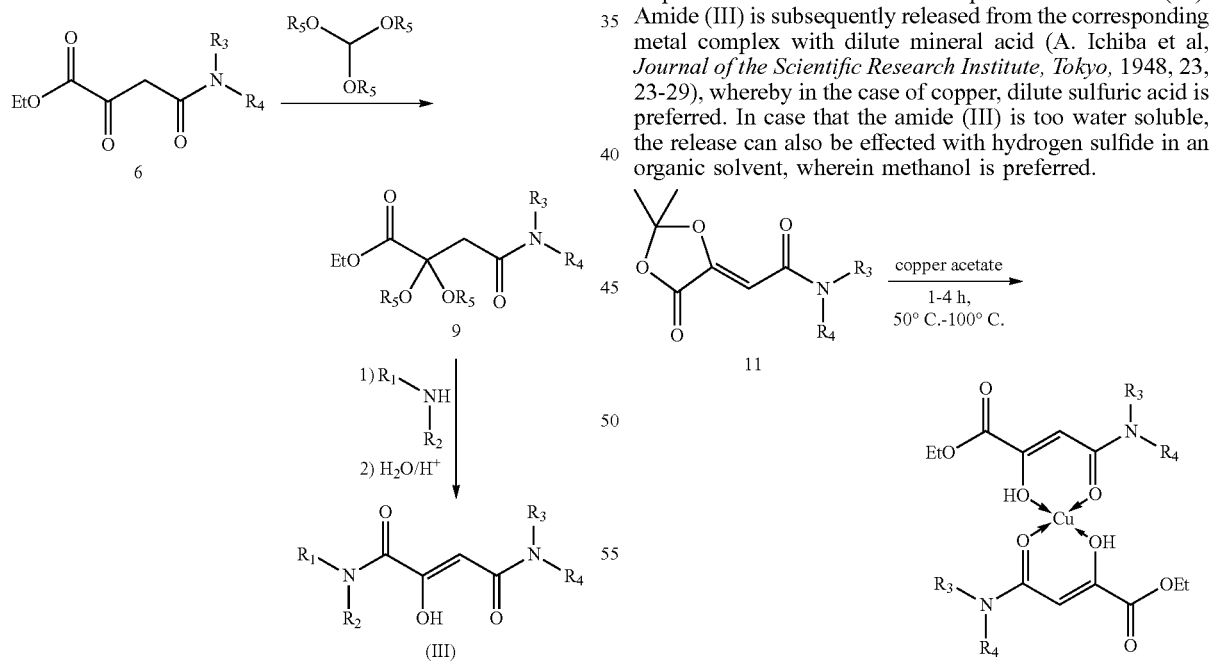

-continued

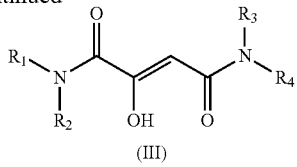

For the fully substituted case ($R_1$, $R_2$, $R_3$, $R_4 \neq H$) the synthesis is simply a classical condensation reaction. Here, commercially available alkyl, N, N-dialkyloxamat 9 and dialkylacetamide 5 is directly reacted with a suitable condensation base to amide (III). As bases various condensation bases are suitable, such as butyllithium, lithium diisopropylamine, sodium, sodium hydride, sodium amide, sodium alkoxides, potassium, potassium hydride, potassium amide and potassium alkoxides, with potassium tert-butoxide being preferred.

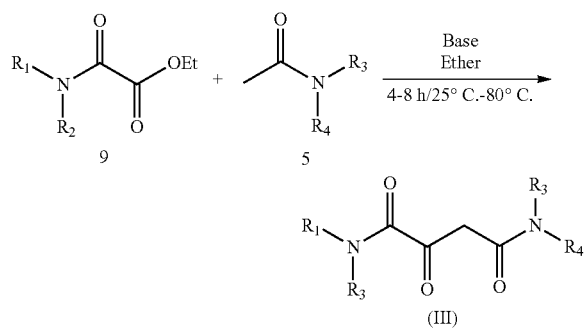

Herein the residues $R_1$ to $R_4$ are as described an das defined above respectively.

Pharmaceutically acceptable salts of the compounds according to the invention, in which the iron(III) complex formally carries a positive charge include, for example, salts with suitable anions, such as carboxylates, sulfonates, sulfates, chlorides, bromides, iodides, phosphates, tartrates, methane sulfonates, hydroxethane sulfonates, glycinates, maleates, propionates, fumarates, toluene sulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention, in which the iron(III) complex formally carries a negative charge include, for example, salts with suitable pharmaceutically acceptable bases, such as, for example, salts with alkaline or alkaline-earth hydroxides, such as NaOH, KOH, $Ca(OH)_2$, $Mg(OH)_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidin, 2-amino-2-methyl-propanol-(1), 2-amino-2-methyl-propandiol-(1,3), 2-amino-2-hydroxyl-methyl-propandiol-(1,3) (TRIS) etc.

The water-solubility or the solubility in physiological saline solution and thus, optionally, also the efficacy of the compounds according to the invention can be significantly influenced by salt formation in general, specifically by the choice of the counter ion.

Preferably, the compounds according to the invention constitute neutral complex compounds.

Advantageous Pharmacological Effects:

Surprisingly, the inventors found that the iron(III) 2-oxo-butanediamide complex compounds, which are the subject matter of the present invention and which are represented, in particular, by the general structural formula (II), are stable bioavailable iron complexes and suitable for use as a medicament for the treatment and prophylaxis of iron deficiency symptoms and iron deficiency anemias and the symptoms accompanying them.

The medicaments containing the compounds according to the invention are suitable for use in human and veterinary medicine.

The compounds according to the invention are thus also suitable for preparing a medicament for the treatment of patients suffering from symptoms of an iron deficiency anemia, such as, for example: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections or depressive moods.

The iron(III) complex compounds according to the invention are furthermore suitable for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CDK 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD). The iron (III) complex compounds of the present invention are also useful for the treatment of iron deficiency with the hemoglobin value being in the normal range. Namely, iron deficiency can occur despite hemoglobin values in the normal range. Generally, the normal range is designated to be the Hb-value range of 96 percent of all healthy people. The normal range of hemoglobin in humans is as follows (see Wikipedia):

|         | g/dl      | mmol/l   |
|---------|-----------|----------|
| male    | 13.5-17.5 | 8.4-10.9 |
| female  | 12-16     | 7.4-9.9  |
| newborn | 19        | 11.8     |

(The determination of the Hb-value can, for example, be carried out according to DIN 58931).

Administration can take place over a period of several months until the iron status is improved, which is reflected, for example, by the hemoglobin level, transferrin saturation and the serum ferritin level of the patients, or until the desired improvement of the state of health affected by iron deficiency anemia.

The preparation according to the invention can be taken by children, adolescents and adults.

The applied compounds according to the invention can in this case be administered both orally as well as parentally. Oral administration is preferred.

The compounds according to the invention and the aforementioned combinations of the compounds according to the invention with other active substances or medicines can thus be used, in particular, for the preparation of medicaments for the treatment of iron deficiency anemia, such as iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), menstruation, injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome.

The application according to the invention leads to an improvement of the iron, hemoglobin, ferritin and transferrin levels, which, in particular in children and adolescents, but also in adults, is accompanied by an improvement in short-term memory tests (STM), long-term memory tests (LTM), Ravens' progressive matrices test, in the Welscher's adult intelligence scale (WAIS) and/or in the emotional coefficient (Baron EQ-i, YV test, youth version), or to an improvement of the neutrophile level, the antibody levels and/or lymphocyte function.

Furthermore, the present invention relates to pharmaceutical compositions comprising one or more of the compounds according to the invention, in particular according to the formula (II), as well as optionally one or more further pharmaceutically effective compounds, as well as optionally one or more pharmacologically acceptable carriers and/or auxiliary substances and/or solvents. The mentioned pharmaceutical compositions contain, for example up to 99 wt-% or up to 90 wt-% or up to 80 wt-% or up to 70 wt-% of the compounds according to the invention, with the remainder in each case being formed by pharmacologically acceptable carriers and/or auxiliaries and/or solvents.

These are common pharmaceutical carriers, auxiliary substances or solvents. The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

In a preferred embodiment of the invention the iron complex compounds are administered in the form of a tablet or capsule. These may be present, for example, as acid resistant forms or with pH dependent coatings.

Preferably, the compounds according to the invention as well as pharmaceutical compositions containing such compounds are applied orally, although other forms, such as parentally, in particular intravenously, are also possible.

For this purpose, the compounds according to the invention are preferably provided in pharmaceutical compositions in the form of pills, tablets, enteric-coated tablets, film tablets, layer tablets, sustained release formulations for oral administration, depot formulations, dragees, granulates, emulsions, dispersions, microcapsules, microformulations, nanoformulations, liposomal formulations, capsules, enteric-coated capsules, powders, microcrystalline formulations, epipastics, drops, ampoules, solutions, suspensions, infusion solutions or injection solutions.

The compounds according to the invention can be administered in pharmaceutical compositions which may contain various organic or inorganic carrier and/or auxiliary materials as they are customarily used for pharmaceutical purposes, in particular for solid medicament formulations, such as, for example, excipients (such as saccharose, starch, mannitol, sorbitol, lactose, glucose, cellulose, talcum, calcium phosphate, calcium carbonate), binding agents (such as cellulose, methylcellulose, hydroxypropylcellulose, polypropyl pyrrolidone, gelatine, gum arabic, polyethylene glycol, saccharose, starch), disintegrating agents (such as starch, hydrolyzed starch, carboxymethylcellulose, calcium salt of carboxymethylcellulose, hydroxypropyl starch, sodium glycol starch, sodium bicarbonate, calcium phosphate, calcium citrate), lubricants (such as magnesium stearate, talcum, sodium laurylsulfate), a flavorant (such as citric acid, menthol, glycin, orange powder), preserving agents (such as sodium benzoate, sodium bisulfite, methylparaben, proylparaben), stabilizers (such as citric acid, sodium citrate, acetic acid and multicarboxylic acids from the titriplex series, such as, for example, diethylenetriaminepentaacetic acid (DTPA), suspending agents (such as methycellulose, polyvinyl pyrrolidone, aluminum stearate), dispersing agents, diluting agents (such as water, organic solvents), beeswax, cocoa butter, polyethylene glycol, white petrolatum, etc.

Liquid medicament formulations, such as solutions, suspensions and gels usually contain a liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected. Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

EXAMPLES

The invention is illustrated in more detail by the following examples. The examples merely constitute exemplifications, and the person skilled in the art is capable of extending the specific examples to other compounds claimed. The designation of the names of the examples were defined and determined using the computer program ACD/Name Version 12.

Starting Compounds:

The starting compounds used in the examples were obtained as follows.

A. $N^4,N^4$-dimethyl-2-oxobutanediamide

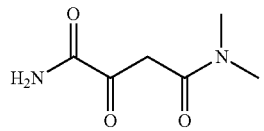

53.30 g (0.475 mol) potassium tert-butoxide are suspended in 300 ml diethyl ether. 73.07 g (0.500 mol) diethyl oxalate have been added under cooling with an ice bath. After 30 min stirring under cooling, 43.57 g (0.500 mol) N,N-dimethylacetamide were added and the reaction mixture was stirred for 2 h. For further processing the solid was filtered and disintegrated in 260 ml 4N hydrochloric acid and 750 ml ethyl acetate. After separation of the phases the aqueous phase was extracted two times with 300 ml ethyl acetate. The combined organic phases were dried over sodium sulfate and evaporated in a rotary evaporator to dryness. The yield of ethyl 4-(dimethylamino)-2,4-dioxobutanoate was 54.3 g (58%).

IR (in substance, $cm^{-1}$): 2984, 2941, 1738, 1620, 1507, 1467, 1393, 1370, 1355, 1313, 1260, 1170, 1126, 1016, 927, 860, 823, 772, 723, 628. $^1$H-NMR (CDCl$_3$, 400 MHz): δ [ppm]=1.38 (3H), 3.06 (6H), 4.33 (2H), 6.25 (1 H).

32.56 g (163.1 mmol) copper acetate monohydrate have been suspended in 470 ml ethanol and heated up to 75° C. 61.06 g (326.2 mmol) ethyl 4-(dimethylamino)-2,4-dioxobutanoate was added in one portion. The mixture was stirred for 40 min at 75° C. The copper complex was precipitated at 4° C. 32.42 g (74.4 mmol) of the copper complex has been suspended in 530 ml methanolic ammonia solution (7N) and stirred at room temperature for 4 h while adding 10 ml ethanol, followed by filtration. For further processing the copper complex was suspended in 960 ml chloroform and stirred at room temperature. 266 ml 10% sulfuric acid have been added stirred for 30 min. The phases have been separated and the aqueous phase has been extracted two times with 960 ml chloroform. The combined organic phases were dried over sodium sulfate and evaporated in a rotary evaporator to dryness. The residue was boiled up with 156 ml ethyl acetate and crystallized over night at 4° C. The crystalline product was filtered and dried under vacuum. The yield of $N^4,N^4$-dimethyl-2-oxobutanediamide was 15.5 g (66%).

IR (in substance, $cm^{-1}$): 3392, 3154, 2950, 2799, 1699, 1633, 1600, 1576, 1502, 1427, 1378, 1344, 1253, 1170, 1122, 1097, 1054, 990, 925, 908, 811, 761, 730, 665.

$^1$H-NMR (DMSO-d$_6$, 400 MHz): δ [ppm]=3.0 (6H), 6.2 (1 H), 7.7 (2H), 15.3 (1 H).

B. 4-(Morpholine-4-yl)-2,4-dioxobutaneamide

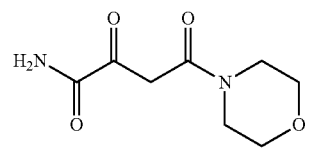 [SMILES: NC(=O)C(=O)CC(=O)N1CCOCC1]

10.2 g diisopropyl amine (0.1 mol) were given in 100 ml dry THF under nitrogen and cooled in a cooling mixture. 40 ml n-buthyllithium in hexane (2.5M, 0.1 mol) were slowly added dropwise. After addition stirring was carried out for 60 min followed by dropwise addition of 12.9 g acetyl morpholine (0.1 mol). The reaction mixture was stirred for further 20 min in the freezing mixture. In a second flask 43.7 g diethyl oxalate (0.3 mol) were cooled in 50 ml dry THF in a freezing mixture and the cold reaction mixture was cannuled in in small portions while stirring. Warming to room temperature was carried out over night while stirring. The THF was evaporated in a rotary evaporator and the residue was collected in 80 ml half concentrated hydrochloric acid. The aqueous phase was extracted five times with 150 ml ethyl acetate in each case, the combined organic phases were dried over sodium sulfate and evaporated in a rotary evaporator to dryness. The excess diethyl oxalate was distilled off (2-3 mbar, 80° C.). 5.0 g ethyl-4-(morpholine-4-yl)-2,4-dioxobutanoate in the form of white crystals with a melting point of 60° C. after crystallization from PE were obtained.

$^1$H-NMR (CDCl$_3$, 400 MHz): δ [ppm]=1.35 (3H), 3.50-3.73 (8H), 4.33 (2H), 6.20 (1 H), 14.32 (1 H).

7.68 g (38.5 mmol) copper acetate monohydrate was suspended in 110 ml ethanol and heated up to 75° C. 17.63 g (76.96 mmol) ethyl-4-(morpholine-4-yl)-2, 4-dioxobutanoate was added in one portion. The mixture was stirred for 15 min at 72° C. Subsequently, 19.86 g of the copper complex were precipitated at 4° C.

15.7 g (30.2 mmol) of the copper complex were suspended in 240 ml methanolic ammonia solution (7N) and stirred for 4 h at room temperature while adding 80 ml ethanol, followed by filtering.

For further processing the copper complex was suspended in 410 ml chloroform and stirred at room temperature. 122 ml 10% sulfuric acid were added followed by stirring for 35 min. The phases were separated and the aqueous phase was extracted twice with 400 ml chloroform. The combined organic phases were dried over sodium sulfate and evaporated in a rotary evaporator to dryness. The residue was boiled up with 80 ml ethyl acetate and crystallized at 4° C. over night. The crystalline product was filtered and dried under vacuum. The yield of 4-(morpholine-4-yl)-2,4-dioxobutaneamide was 5.3 g (34%).

IR (in substance, $cm^{-1}$): 3453, 3342, 3285, 3180, 2985, 2932, 2873, 1716, 1635, 1576, 1485, 1463, 1442, 1381, 1330, 1303, 1272, 1243, 1195, 1132, 1103, 1066, 1049, 978, 940, 905, 850, 819, 795, 767, 726, 665.

Enol form $^1$H-NMR (DMSO-d$_6$, 400 MHz): δ [ppm]=3.6 (4H), 6.2 (1 H), 7.8 (2H), 15.0 (1 H).

C. N$^4$,N$^4$-diethyl-2-oxobutanediamide

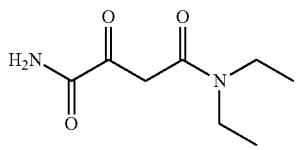

18.5 g (0.165 mol) sodium tert-butoxide was suspended in 100 ml diethyl ether. 25.4 g (0.174 mol) diethyl oxalate were added under cooling in an ice bath. Stirring was carried out for 30 min under cooling, 20.0 g (0.174 mol) N,N-diethylacetamide were added and the reaction mixture was stirred at room temperature over night. For further processing 260 ml diethyl ether were added and the solid filtered. The solid was disintegrated in 35 ml 6N hydrochloric acid, 174 ml ethyl acetate and 20 ml water. After phase separation the aqueous phase was extracted two more times with 100 ml ethyl acetate. The combined organic phases were dried over sodium sulfate and evaporated in a rotary evaporator to dryness. The raw product was crystallized from petroleum ether/diethyl ether at 4° C. The yield of ethyl 4-(diethylamino)-2,4-dioxobutanoate was 17.6 g (47%).

Enol form $^1$H-NMR (CDCl3, 400 MHz): δ [ppm]=1.2 (6H), 1.4 (3H), 3.4 (4H), 4.4 (2H), 6.2 (1 H)

8.16 g (40.9 mmol) copper acetate monohydrate was suspended in 100 ml ethanol and heated up to 73° C. 17.6 g (81.7 mmol) ethyl 4-(diethylamino)-2,4-dioxobutanoate were added in one portion. The mixture was stirred for 40 min at 72° C. Subsequently, 50 ml toluene were added and the solvent removed at the rotary evaporator. The residue was evaporated with 50 ml toluene two more times. 19.9 g of the copper complex were obtained as the raw product and further used without additional purification.

9.0 g (18 mmol) of the copper complex were dissolved in 25 ml methanolic ammonia solution (7N) and stirred for 4 h at room temperature. Subsequently, the solvent was completely removed at the rotary evaporator. For further processing the copper complex was suspended in 190 ml dichloromethane and stirred at room temperature. 53 ml 10% sulfuric acid were added and stirring was carried out for 5 min. The phases were separated and the aqueous phase was extracted two more times with 90 ml dichloromethane. The combined organic phases were dried over sodium sulfate and evaporated in a rotary evaporator to dryness. The residue was purified using column chromatography (silica gel, ethyl acetate). The yield of N$^4$,N$^4$-diethyl-2-oxobutanediamide was 6.3 g (94%).

IR (in substance, cm$^{-1}$): 3371, 3193, 2974, 2935, 2875, 2324, 2051, 1982, 1787, 1741, 1683, 1635, 1586, 1495, 1459, 1400, 1380, 1362, 1308, 1269, 1239, 1218, 1158, 1130, 1098, 1081, 1048, 960, 896, 827, 782.

Enol form $^1$H-NMR (DMSO-d$_6$, 400 MHz): δ [ppm]=1.1 (6H), 3.4 (4H), 6.1 (1 H), 7.8 (2H), 15.4 (1 H).

D. 2,4-Dioxo-4-(pyrrolidine-1-yl)butaneamide

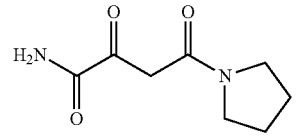

8.33 g (74.4 mmol) sodium tert-butoxide were suspended in 47 ml diethyl ether. 11.4 g (78.3 mmol) diethyl oxalate were added under cooling in an ice bath. Stirring was carried out for 60 min under cooling, 8.86 g (78.3 mmol) N-acetyl pyrrolidine were added and the reaction mixture was stirred for three hours at room temperature. The suspension was filtered off. The solid was disintegrated in 25 ml 6N hydrochloric acid, 120 ml ethyl acetate and 15 ml water. After separation of the phases the aqueous phase was extracted with 50 ml ethyl acetate two times more. The combined organic phases were dried over sodium sulfate and evaporated in a rotary evaporator to dryness. The raw product was purified using column chromatography (silica gel, petroleum ether, ethyl acetate 2/1). The yield of ethyl 2,4-dioxo-4-(pyrrolidine-1-yl)butanoate was 7.7 g (46%).

Enol form $^1$H-NMR (DMSO-d$_6$, 400 MHz): δ [ppm]=1.3 (3H), 1.9 (4H), 3.4 (2H), 3.5 (2H), 4.3 (2H), 6.1 (1 H), 14.9 (1 H).

3.59 g (18.0 mmol) copper acetate monohydrate were suspended in 10 ml ethanol and heated up to 73° C. 7.66 g (35.9 mmol) ethyl 2,4-dioxo-4-(pyrrolidine-1-yl)butanoate were added in one portion. The mixture was stirred for 30 min at 72° C. Subsequently, 20 ml ethanol and 10 ml water were added and stirred for further 20 minutes. After hot filtering the solution was stored at 4° C. The combined organic phases were dried over sodium sulfate and evaporated in a rotary evaporator to dryness. 4.4 g of the copper complex were obtained in crystalline form and further used without further purification. 4.4 g (9.0 mmol) of the copper complex were dissolved in 64 ml methanolic ammonia solution (7N) and stirred for 4 h at room temperature. The suspension was filtered and the solid dried for 3 days at 50° C. in fine vacuum. For further processing the copper complex was suspended in 100 ml dichloromethane and 53 ml 10% sulfuric acid were added. Stirring was carried out until two clear phases developed. The phases were separated and the aqueous phase was extracted for two further times with 100 ml dichloromethane. The combined organic phases were dried over sodium sulfate and evaporated in a rotary evaporator to dryness. The residue was crystallized from hot ethyl acetate. The yield of 2,4-dioxo-4-(pyrrolidine-1-yl) butaneamide was 1.7 g (51%).

IR (in substance, cm$^{-1}$): 3444, 3293, 3146, 2976, 2890, 1688, 1628, 1586, 1482, 1460, 1399, 1343, 1301, 1230, 1187, 1164, 1128, 1107, 1052, 1019, 970, 913, 852, 819, 748.

Enol form $^1$H-NMR (DMSO-d$_6$, 400 MHz): δ [ppm]=1.9 (4H), 3.4 (4H), 6.0 (1 H), 7.8 (2H), 15.3 (1 H).

E. N,N,N',N'-Tetramethyl-2-oxobutanediamide

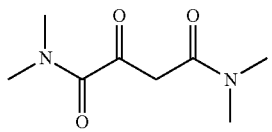

18.65 g (166.3 mmol) sodium tert-butoxide were suspended in 170 ml diethyl ether. 25.58 g (175.0 mmol) ethyl N,N-dimethyloxamate were added while cooling with an ice bath. Stirring was carried out for 30 min and the combined organic phases were dried over sodium sulfate and evaporated in a rotary evaporator to dryness. 15.25 g (175.0 mmol) N,N-dimethyl acetamide were added and the reaction mixture stirred at room temperature for two hours. To the reaction mixture 90 ml 6N hydrochloric acid, 420 ml ethyl acetate and 15 ml water were added and stirred for five minutes. After separation of the phases the aqueous phase was extracted with 200 ml ethyl acetate. The combined organic phases were dried over sodium sulfate and evaporated in a rotary evaporator to dryness. The raw product was purified using column chromatography (silica gel, dichloromethane/acetone 5/1). The yield of N,N,N',N'-tetramethyl-2-oxobutanediamide was 5.3 g (16%).

IR (in substance, cm$^{-1}$): 2936, 1720, 1635, 1496, 1456, 1397, 1352, 1259, 1237, 1203, 1130, 1107, 1077, 951, 892, 849, 807, 774, 753, 720.
Keto form
$^1$H-NMR (DMSO-d$_6$, 400 MHz): δ [ppm]=2.8-3.0 (12H), 3.9 (2H).

F. 4-(4-Hydroxypiperidine-1-yl)-2,4-dioxobutaneamide

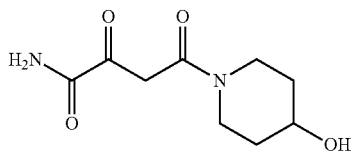 [SMILES: NC(=O)C(=O)CC(=O)N1CCC(O)CC1]

120 g (1.19 mol) 4-hydroxypyridine were dissolved in 1700 ml dichloromethane and 132 g (1.03 mol) triethylamine were added dropwise. The reaction mixture was cooled to −40° C. and 93.4 g (1.19 mol) acetyl chloride was added dropwise. Subsequently, stirring was carried out at room temperature for one hour. The suspension was filtered and the filtrate concentrated at the rotary evaporator until dryness. The residue was collected in 1700 ml ethyl acetate and filtered again. The filtrate was concentrated until dryness. As product 120 g (71%) 1-(4-hydroxypiperidine-1-yl)ethanone were obtained.

$^1$H-NMR (CDCl$_3$, 400 MHz): δ [ppm]=1.5 (2H), 1.8 (2H), 2.1 (3H), 2.7 (1 H), 3.2 (2H), 3.7 (1 H), 3.9 (1 H), 4.1 (1 H).

120 g (839 mmol) 1-(4-hydroxypiperidine-1-yl) ethanone were suspended in 1.51 dichloromethane and cooled in an ice bath. 85.9 g (839 mmol) triethylamine were added dropwise and stirred for 10 minutes. Subsequently, 101 g (839 mmol) trimethyl acetyl chloride were added and the reaction mixture stirred at room temperature for three days. The reaction mixture was concentrated to 200 ml and filtered. Subsequently, the filtrate was concentrated until dryness. The residue was collected in 200 ml ethyl acetate and stirred for 30 minutes. After filtering the filtrate was concentrated at the rotary evaporator until dryness. For purification the product was crystallized from n-heptane. 56 g (29%) 1-acetylpiperidine-4-yl-2,2-dimethylpropanoate in the form of white crystals were obtained.

$^1$H-NMR (CDCl$_3$, 400 MHz): δ [ppm]=1.2 (9 H), 1.6 (2H), 1.8 (2H), 2.1 (3H), 3.4 (1 H), 3.6 (2H), 3.7 (1 H), 5.0 (1 H).

9.88 g (88.0 mmol) sodium tert-butoxide were suspended in 80 ml diethyl ether and 12.9 g (88.0 mmol) diethyl oxalate were added. 20.0 g (88.0 mmol) 1-acetylpiperidine-4-yl-2,2-dimethylpropanoate were dissolved in 80 ml diethyl ether and dropwise added to the reaction mixture. Stirring was carried out for 20 min and subsequently the mixture was left without stirring over night. For further processing 160 ml petroleum ether were added and the suspension filtered off. The residue was collected in 60 ml 1N HCl and pH 7 was adjusted with sodium hydroxide solution. Subsequently, extraction with 200 ml ethyl acetate was carried out three times, drying over sodium sulfate and concentration until dryness at the rotary evaporator. 15.3 g (53%) ethyl-4-{4-[(2,2-dimethylpropanoyl)oxy]piperidine-1-yl}-2,4-dioxobutanoate were obtained. The said was further processed without further purification.
Enol form
$^1$H-NMR (DMSO-d$_6$, 400 MHz): δ [ppm]=1.2 (9H), 1.4 (3H), 1.7 (2H), 1.9 (2H), 3.5-3.8 (4H), 4.3 (2H), 5.0 (1 H), 6.3 (1 H), 14.5 (1 H).

189 g (577 mmol) ethyl-4-{4-[(2,2-dimethylpropanoyl)oxy]piperidine-1-yl}-2,4-dioxobutanoate were dissolved in 900 ml dry ethanol and heated up to 50° C. 393 g 21% sodium ethoxide solution (1.21 mol) were added dropwise and stirred at 50° C. over night. The reaction mixture was concentrated at the rotary evaporator until dryness and the residue collected in 21 1N hydrochloric acid. Extraction with 21 ethyl acetate was carried out three times, dried over sodium sulfate and concentrated until dryness. The raw product was purified using column chromatography (silica gel, acetone/dichloromethane 1/1). 74.9 g (53%) ethyl 4-(4-hydroxypiperidine-1-yl)-2,4-dioxobutanoate were obtained.
Enol form
$^1$H-NMR (DMSO-d$_6$, 400 MHz): δ [ppm]=1.3 (3H), 1.4 (2H), 1.8 (2H), 3.3 (2H), 3.7 (1 H), 3.8 (2H), 4.2 (2H), 4.8 (1 H), 6.3 (1 H), 14.9 (1 H). 8.78 g (44.0 mmol) copper acetate monohydrate were suspended in 125 ml ethanol and heated until boiling. 21.3 g (88.0 mmol) ethyl 4-(4-hydroxypiperidine-1-yl)-2,4-dioxobutanoate were added in portions. The mixture was boiled under reflux for 40 min. After filtering the solution was stored at 2.2° C. over night. 13.2 g of the copper complex were obtained in crystalline form and used for further processing without further purification.

7.18 g (13.8 mmol) of the copper complex were dissolved in 98 ml methanolic ammonia solution (7N) and stirred for 4 h at room temperature. The suspension was filtered and the residue dried at 50° C. under fine vacuum. For further processing the copper complex was suspended in 125 ml methanol and H$_2$S was conducted through the suspension for 30 min. Stirring was carried out until two clear phases developed. Filtering over Celite® was carried out two times followed by concentration of the filtrate at the rotary evaporator.

The residue was recrystallized in ethyl acetate. The yield of 4-(4-hydroxypiperidine-1-yl)-2,4-dioxobutaneamide was 0.5 g (8%). IR (in substance, cm$^{-1}$): 3282, 3118, 2981, 2324, 2164, 2051, 1981, 1797, 1546, 1413, 1349, 1264, 1161, 1138, 1086, 1043, 962, 925, 899, 821, 786, 728, 676.
Enol form
$^1$H-NMR (DMSO-d$_6$, 400 MHz): δ [ppm]=1.3 (2H), 1.7 (2H), 3.3 (2H), 3.7-3.9 (3H), 4.8 (1 H), 6.2 (1 H), 7.7 (2H), 15.3 (1 H).

G. N$^1$,N$^4$,N$^4$-Trimethyl-2-oxobutanediamide

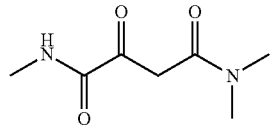

53.30 g (0.475 mol) sodium tert-butoxide were suspended in 300 ml diethyl ether. 73.07 g (0.500 mol) diethyl oxalate were added under cooling in an ice bath. Stirring was carried out for 30 min under cooling, 43.57 g (0.500 mol) N,N-di methylacetamide were added and the reaction mixture stirred for 2 h. For further processing was filtered off and the solid disintegrated in 260 ml 4N hydrochloric acid and 750 ml ethyl acetate. After separation of the phases the aqueous phase was extracted with 300 ml ethyl acetate two more times. The combined organic phases were dried over sodium sulfate and evaporated in a rotary evaporator to dryness. The yield of ethyl 4-(dimethylamino)-2,4-dioxobutanoate was 54.3 g (58%).
$^1$H-NMR (CDCl3, 400 MHz): δ [ppm]=1.38 (3H), 3.06 (6H), 4.33 (2H), 6.25 (1 H)
32.56 g (163.1 mmol) copper acetate monohydrate was suspended in 470 ml ethanol and heated up to 75° C. 61.06 g (326.2 mmol) ethyl 4-(dimethylamino)-2,4-dioxobutanoate was added in one portion. The mixture was stirred for 40 min at 75° C. The copper complex was precipitated at 4° C. 10.0 g (23.0 mmol) of the copper complex were suspended in 57 ml ethanolic methylamine solution (33%) and stirred at room temperature for 2 h. The reaction mixture was concentrated until dryness. For further processing the copper complex was dissolved in 100 ml chloroform. 170 ml 10% sulfuric acid were added and both phases were stirred thoroughly. After separation of the phases the aqueous phase was extracted with 50 ml chloroform two more times. The combined organic phases were dried over sodium sulfate and concentrated in a rotary evaporator until dryness. The yield of N$^1$,N$^4$,N$^4$-trimethyl-2-oxobutanediamide was 4.1 g (52%). IR (in substance, cm$^{-1}$): 3398, 3315, 3105, 2931, 2324, 1783, 1671, 1632, 1599, 1526, 1500, 1405, 1361, 1347, 1252, 1160, 1063, 1018, 935, 907, 838, 776, 726.
Enol form:
$^1$H-NMR (DMSO-d$_6$, 400 MHz): δ [ppm]=2.7 (3H), 3.0 (6H), 6.1 (1 H), 8.4 (1 H), 15.5 (1 H).

H. N,N'-Dimethyl-2-oxobutanediamide

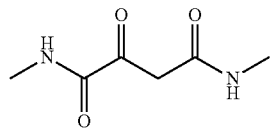

38.2 g (0.556 mol) methylamine hydrochloride were suspended in 70 ml dichloromethane and 57.3 g (0.556 mol) triethylamine were added. The reaction mixture was cooled to −60° C. and 108 g (0.556 mol) (2Z)-(2,2-dimethyl-5-oxo-1,3-dioxolane-4-yliden)acetyl chloride (prepared according to J. Banville et al, *Tetrahedron Letters,* 2010, 51, 3170-3173), dissolved in 70 ml dichloromethane, were added dropwise. Subsequently, stirring was carried out over night at room temperature and finally boiled for four hours under reflux. The reaction mixture was concentrated until dryness and the residue was collected in 400 ml ethyl acetate. The suspension was filtered and the filtrate concentrated until dryness. The residue was collected in 600 ml diethyl ether. The suspension was filtered and the filtrate concentrated until dryness. 49.1 g (47%) (2Z)-(2,2-dimethyl-5-oxo-1,3-dioxolane-4-yliden)-N-methylacetamide were obtained.
$^1$H-NMR (DMSO-d$_6$, 400 MHz): δ [ppm]=1.7 (6H), 2.6 (3H), 5.8 (1 H), 8.0 (1 H).
13.1 g (66.0 mmol) copper acetate monohydrate were suspended in 600 ml ethanol and 25.7 g (132 mmol) (2Z)-(2,2-dimethyl-5-oxo-1,3-dioxolane-4-yliden)-N-methylacetamide were added. The mixture was boiled for four hours under reflux. The suspension was concentrated until dryness and the residue stripped with toluene three times to remove the acetic acid. 10.6 g (25.9 mmol) of the copper complex were suspended in 31 ml ethanolic methylamine solution (33%) and stirred for 2 hours at room temperature. The reaction mixture was concentrated until dryness. For further processing the copper complex was dissolved in 200 ml dichloromethane. 60 ml 10% sulfuric acid and 30 ml water were added and the two phases were stirred thoroughly. After separation of the phases the aqueous phase was extracted with 100 ml dichloromethane two times. The combined organic phases were dried over sodium sulfate and concentrated in a rotary evaporator until dryness. The product was crystallized from hot ethyl acetate. The yield of N,N'-dimethyl-2-oxobutanediamide was 0.4 g (5%).
IR (in substance, cm$^{-1}$): 3367, 3310, 3133, 2942, 2051, 1624, 1584, 1532, 1396, 1275, 1247, 1133, 1078, 946, 838, 776, 752, 674.
Enol form:
$^1$H-NMR (DMSO-d$_6$, 400 MHz): δ [ppm]=2.7 (6H), 5.9 (1 H), 8.4 (2H), 14.3 (1 H).

I. N$^1$,N$^1$,N$^4$-Trimethyl-2-oxobutanediamide

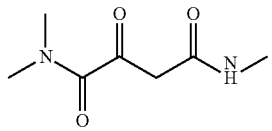

38.2 g (0.556 mol) methylamine hydrochloride was suspended in 70 ml dichloromethane and 57.3 g (0.556 mol) triethylamine were added. The reaction mixture was cooled to −60° C. and 108 g (0.556 mol) (2Z)-(2,2-dimethyl-5-oxo-1,3-dioxolane-4-yliden)acetyl chloride (prepared according to J. Banville et al, *Tetrahedron Letters,* 2010, 51, 3170-3173) dissolved in 70 ml dichloromethane were added dropwise. Subsequently, stirring at room temperature was carried out over night and finally was boiled for four hours under reflux. The reaction mixture was concentrated until dryness and the residue collected in 400 ml ethyl acetate. The suspension was filtered and the filtrate concentrated until dryness. The residue was collected in 600 ml diethyl ether. The suspension was filtered and the filtrate concentrated until dryness. 49.1 g (47%) (2Z)-(2,2-dimethyl-5-oxo-1,3-dioxolane-4-yliden)-N-methylacetamide were obtained.

$^1$H-NMR (DMSO-d$_6$, 400 MHz): δ [ppm]=1.7 (6H), 2.6 (3H), 5.8 (1 H), 8.0 (1 H).

1.0 g (5.4 mmol) (2Z)-(2,2-dimethyl-5-oxo-1,3-dioxolane-4-yliden)-N-methylacetamide were dissolved in 9.6 ml ethanolic dimethylamine solution (33%) and stirred at room temperature for five minutes. 6 ml 6N hydrochloric acid were added and stirred again for five minutes. The reaction mixture was concentrated until dryness and the residue was collected in 15 ml water. The aqueous phase was extracted twice with 50 ml ethyl acetate. The combined organic phases were dried over sodium sulfate and concentrated in a rotary evaporator until dryness. The raw product was purified using column chromatography (silica gel, ethyl acetate). The yield of N$^1$,N$^1$,N$^4$-trimethyl-2-oxobutanediamide was 280 mg (30%).

IR (in substance, cm$^{-1}$): 3303, 3099, 2941, 1766, 1719, 1624, 1561, 1502, 1449, 1405, 1338, 1255, 1227, 1160, 1079, 1041, 947, 910, 829, 773, 657.

Keto form:

$^1$H-NMR (DMSO-d$_6$, 400 MHz): δ [ppm]=2.6 (3H), 2.9 (6H), 3.6 (2H), 8.1 (1 H).

J. N$^4$,N$^4$-diethyl-N$^1$,N$^1$-dimethyl-2-oxobutanediamide

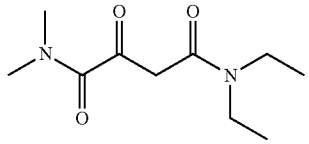

8.0 g (71 mmol) sodium tert-butoxide were suspended in 60 ml diethyl ether. 10.9 g (75.0 mmol) ethyl N,N-dimethyl oxamate were added under cooling in an ice bath. Stirring was carried out for 30 min at room temperature, 8.6 g (75 mmol) N,N-diethylacetamide were added and the reaction mixture was stirred at room temperature for two hours. 45 ml 6N hydrochloric acid, and 200 ml ethyl acetate were added to the reaction mixture. After separation of the phases the aqueous phase was extracted with 50 ml ethyl acetate for two further times. The combined organic phases were dried over sodium sulfate and concentrated in a rotary evaporator until dryness. The raw product was purified using column chromatography (silica gel, petroleum ether/ethyl acetate). The yield of N$^4$,N$^4$-diethyl-N$^1$,N$^1$-dimethyl-2-oxobutanediamide was 3.5 g (22%).

IR (in substance, cm$^{-1}$): 3496, 2975, 2936, 1721, 1626, 1487, 1448, 1400, 1380, 1362, 1308, 1271, 1217, 1200, 1141, 1100, 1077, 954, 927, 789, 771, 734.

Keto form $^1$H-NMR (DMSO-d$_6$, 400 MHz): δ [ppm]=1.1 (6H), 3.0 (6H), 3.3 (4H), 3.9 (2H).

K. N,N-Dimethyl-3,4-dioxo-4-(pyrrolidine-1-yl)butaneamide

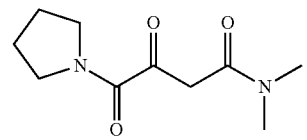

19.2 g (270 mmol) pyrrolidine and 27.3 g (270 mmol) triethylamine were dissolved in 400 ml diethyl ether and cooled in an ice bath. 36.9 g (270 mmol) ethyl chlorooxoacetate were added dropwise followed by heating until room temperature. The suspension was filtered and the filtrate concentrated at the rotary evaporator. 46.6 g ethyloxo(pyrrolidine-1-yl)acetate in the form of a yellow oil were obtained and used for further processing without further purification.

27.2 g (242 mmol) sodium tert-butoxide were suspended in 200 ml diethyl ether. 43.6 g (255 mmol) ethyl-oxo(pyrrolidine-1-yl)acetate were added under cooling in an ice bath. Stirring was carried out for 30 min at room temperature, 22.2 g (255 mmol) N,N-dimethylacetamide were added and the reaction mixture was stirred at room temperature for two hours. 136 ml 6N hydrochloric acid, 170 ml ethyl acetate and 70 ml water were added to the reaction mixture. After separation of the phases the aqueous phase was extracted with 100 ml ethyl acetate two times. The combined organic phases were dried over sodium sulfate and concentrated in a rotary evaporator until dryness. The raw product was purified using column chromatography (silica gel, petroleum ether/ethyl acetate). The yield of N,N-dimethyl-3,4-dioxo-4-(pyrrolidine-1-yl)butaneamide was 37.1 g (69%).

IR (in substance, cm$^{-1}$): 2952, 2880, 1722, 1632, 1602, 1503, 1445, 1415, 1354, 1338, 1253, 1224, 1163, 1141, 1060, 1033, 975, 952, 915, 890, 870, 848, 812, 765, 728, 695.

Enol form $^1$H-NMR (DMSO-d$_6$, 400 MHz): δ [ppm]=1.8 (4H), 3.0 (6H), 3.4 (2H), 3.6 (2H), 5.9 (1 H), 15.6 (1 H).

L. N$^4$-[2-(Dimethylamino)-2-oxoethyl]-N$^1$,N$^1$,N$^4$-trimethyl-2-oxobutanediamide

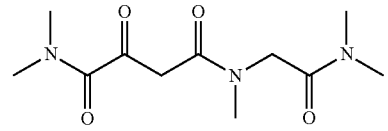

17.1 g (0.112 mol) N,N-dimethyl-2-(methylamino)acetamide hydrochloride (Sigma-Aldrich: CDS007544) was suspended in 300 ml dichloromethane and 22.6 g (0.224 mol) triethylamine were added. 21.3 g (0.112 mol) (2Z)-(2,2-dimethyl-5-oxo-1,3-dioxolane-4-yliden)acetyl chloride (prepared according to J. Banville et al, *Tetrahedron Letters*, 2010, 51, 3170-3173) were added in portions. Subsequently, stirring was carried out for 30 minutes at room temperature, followed by boiling under reflux for four hours. The suspension was concentrated until dryness and the residue collected in 300 ml ethyl acetate. The suspension was filtered and the filtrate concentrated until dryness. 9.8 g (32%) N²-[(2Z)-2-(2,2-dimethyl-5-oxo-1,3-dioxolane-4-yliden)acetyl]-N,N,N²-trimethylglycineamide were obtained.

¹H-NMR (DMSO-d₆, 400 MHz): δ [ppm]=1.7 (6H), 2.8-3.0 (9H), 4.2-4.3 (2H), 5.8-6.1 (1 H).

8.8 g (32 mmol) N²-[(2Z)-2-(2,2-dimethyl-5-oxo-1,3-dioxolane-4-yliden)acetyl]-N,N,N²-trimethylglycineamide were dissolved in 58 ml ethanolic dimethylamine solution (33%) and stirred at room temperature for 30 minutes. The reaction mixture was concentrated until dryness. The raw product was purified using column chromatography (silica gel, dichloremethane:methanol 20:1). The yield of N⁴-[2-(dimethylamino)-2-oxoethyl]-N¹,N¹,N⁴-trimethyl-2-oxobutanediamide was 3.0 g (36%).

IR (in substance, cm⁻¹): 3492, 2936, 1720, 1631, 1492, 1398, 1364, 1332, 1261, 1239, 1217, 1139, 1106, 1078, 951, 898, 860, 812, 762, 720, 675.

Keto form:

¹H-NMR (DMSO-d₆, 400 MHz): δ [ppm]=2.7-3.0 (15H), 3.7-4.0 (2H), 4.1-4.3 (2H).

M. N⁴-(2-Methoxyethyl)-N¹,N¹,N⁴-trimethyl-2-oxobutanediamide

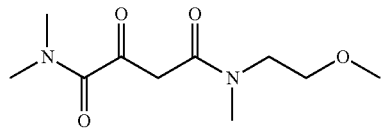

9.09 g (102 mmol) (2-methoxyethyl)methylamine and 10.3 g (102 mmol) triethylamine were dissolved in 110 ml diethyl ether and cooled in an ice bath. 8.01 g (102 mmol) acetyl chloride were added dropwise followed by heating to room temperature. The suspension was filtered and the filtrate concentrated at the rotary evaporator. 10 g N-(2-methoxyethyl)-N-methylacetamide in the form of a colourless oil were obtained, was used for further processing without further purification. 8.08 g (72.0 mmol) sodium tert-butoxide were suspended in 100 ml diethyl ether. 10.5 g (72.0 mmol) ethyl N,N-dimethyloxamate were added under cooling in an ice bath. Stirring was carried out for 15 min at room temperature, 9.44 g (72.0 mmol) N-(2-methoxyethyl)-N-methylacetamide were added and the reaction mixture was stirred at room temperature for two hours. 140 ml 6N hydrochloric acid, 180 ml ethyl acetate and 45 ml water were added to the reaction mixture. After separation of the phases the aqueous phase was extracted with 80 ml ethyl acetate three times. The combined organic phases were dried over sodium sulfate and concentrated in a rotary evaporator until dryness. The raw product was purified using column chromatography (silica gel, petroleum ether/ethyl acetate). The yield of N⁴-(2-methoxyethyl)-N¹,N¹,N⁴-trimethyl-2-oxobutanediamide was 2.98 g (18%).

IR (in substance, cm⁻¹): 2935, 1612, 1498, 1458, 1427, 1362, 1260, 1193, 1153, 1114, 1062, 1022, 950, 842, 814, 787, 724, 694, 674.

Keto form

¹H-NMR (DMSO-d₆, 400 MHz): δ [ppm]=2.8-3.0 (9H), 3.2-3.3 (3H), 3.4-3.6 (4H), 3.9-4.0 (2H).

N. N⁴-(2-Methoxyethyl)-N¹,N¹-dimethyl-2-oxobutanediamide

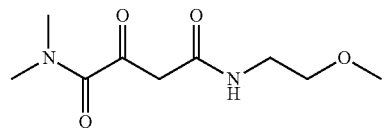

7.1 g (94 mmol) 2-methoxyethylamine were suspended in 300 ml dichloromethane and 19.0 g (188 mmol) triethylamine were added. 18.0 g (94 mmol) (2Z)-(2,2-dimethyl-5-oxo-1,3-dioxolane-4-yliden)acetyl chloride (prepared according to J. Banville et al, *Tetrahedron Letters*, 2010, 51, 3170-3173) dissolved in 70 ml dichloromethane. Subsequently, stirring was carried out for 30 minutes at room temperature followed by boiling under reflux for four hours. The suspension was concentrated until dryness and the residue was collected in 300 ml ethyl acetate. The suspension was filtered and the filtrate concentrated until dryness. The residue was collected in 350 ml diethyl ether and stirred. The suspension was filtered and the filtrate concentrated until dryness. 15.4 g (71%) (2Z)-2-(2,2-dimethyl-5-oxo-1,3-dioxolane-4-yliden)-N-(2-methoxyethyl)acetamide were obtained.

¹H-NMR (DMSO-d₆, 400 MHz): δ [ppm]=1.7 (6H), 3.3 (3H), 3.3-3.4 (4H), 5.9 (1 H), 8.2 (1 H).

3.0 g (13 mmol) (2Z)-2-(2,2-Dimethyl-5-oxo-1,3-dioxolan-4-yliden)-N-(2-methoxyethyl)acetamide were dissolved in 23 ml ethanolic dimethylamine solution (33%) and stirred at room temperature for 5 minutes. 18 ml 6N HCl-solution were added, stirred for 5 minutes and concentrated at the rotary evaporator until dryness. The yield of N⁴-(2-methoxyethyl)-N¹,N¹-dimethyl-2-oxobutanediamide was 2.3 g (82%).

IR (in substance, cm⁻¹): 3307, 3086, 2932, 2884, 1720, 1634, 1548, 1503, 1452, 1401, 1324, 1266, 1195, 1121, 1084, 1041, 948, 819, 772, 718.

Keto form:

¹H-NMR (DMSO-d₆, 400 MHz): δ [ppm]=2.9 (6H), 3.3 (3H), 3.2-3.4 (4H), 3.6 (2H), 8.2 (1 H).

O. ethyl-N-[4-(dimethylamino)-3,4-dioxobutanoyl]-N-methylglycinate

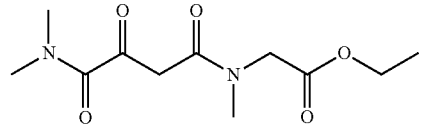 [SMILES: CCOC(=O)CN(C)C(=O)CC(=O)C(=O)N(C)C]

15.0 g (97.7 mmol) sarcosine ethylester hydrochloride were suspended in 300 ml dichloromethane and 19.8 g (195 mmol) triethylamine were added. 18.8 g (98.7 mmol) (2Z)-(2,2-dimethyl-5-oxo-1,3-dioxolane-4-yliden)acetyl chloride (prepared according to J. Banville et al, *Tetrahedron Letters*, 2010, 51, 3170-3173) dissolved in 70 ml dichloromethane were added. Subsequently, stirring was carried out for 30 minutes at room temperature followed by boiling under reflux for four hours. The suspension was concentrated until dryness and the residue collected in 300 ml ethyl acetate. The suspension was filtered and the filtrate concentrated until dryness. 12 g (45%) ethyl-N-[(2Z)-2-(2,2-dimethyl-5-oxo-1,3-dioxolane-4-yliden)acetyl]-N-methylglycinate were obtained.

$^1$H-NMR (DMSO-d$_6$, 400 MHz): δ [ppm]=1.2 (3H), 1.8 (6H), 3.1 (3H), 4.1 (2H), 4.1-4.3 (2H).

3.0 g (11 mmol) ethyl-N-[(2Z)-2-(2,2-dimethyl-5-oxo-1,3-dioxolane-4-yliden)acetyl]-N-methylglycinate were dissolved in 20 ml ethanolic dimethylamine solution (33%) and stirred for 5 minutes at room temperature. 18 ml 6N HCl-solution were added, stirring was carried out for 5 minutes and the reaction mixture was concentrated until dryness. The residue was collected in 50 ml water and extracted with 150 ml ethyl acetate three times. The combined organic phases were dried over sodium sulfate. The yield of ethyl-N-[4-(dimethylamino)-3,4-dioxobutanoyl]-N-methylglycinate was 2.3 g (81%).

IR (in substance, cm$^{-1}$): 2938, 1743, 1638, 1489, 1399, 1374, 1354, 1197, 1107, 1077, 1031, 950, 900, 851, 811, 765, 717.

Keto form:
$^1$H-NMR (DMSO-d$_6$, 400 MHz): δ [ppm]=1.2 (3H), 2.8-3.1 (9H), 3.8-4.0 (2H), 4.1 (2H), 4.1-4.3 (2H).

P. $N^1$-(2-Methoxyethyl)-$N^4$,$N^4$-dimethyl-2-oxobutaneamide

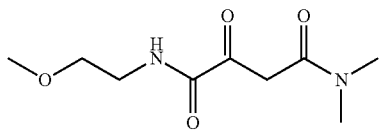

53.30 g (0.475 mol) sodium tert-butoxide were suspended in 300 ml diethyl ether. 73.07 g (0.500 mol) diethyl oxalate were added under cooling in an ice bath. Stirring was carried out for 30 min, 43.57 g (0.500 mol) N,N-dimethylacetamide were added and the reaction mixture was stirred for 2 h. For further processing was filtered and the solid disintegrated in 260 ml 4N hydrochloric acid and 750 ml ethyl acetate. After separation of the phases the aqueous phase was extracted with 300 ml ethyl acetate two times. The combined organic phases were dried over sodium sulfate and concentrated in a rotary evaporator until dryness. The yield of ethyl 4-(dimethylamino)-2,4-dioxobutanoaet was 54.3 g (58%).

$^1$H-NMR (CDCl3, 400 MHz): δ [ppm]=1.38 (3H), 3.06 (6H), 4.33 (2H), 6.25 (1 H)

32.56 g (163.1 mmol) copper acetate monohydrate were suspended in 470 ml ethanol and heated up to 75° C. 61.06 g (326.2 mmol) ethyl 4-(dimethylamino)-2,4-dioxobutanoate were added in one portion. The mixture was stirred for 40 min at 75° C. The copper complex was precipitated at 4° C.

10.0 g (22.9 mmol) of the copper complex were dissolved in 40 ml ethanol, 17.2 g (229 mmol) 2-methoxyethylamine were added and stirred for two hours at room temperature. Subsequently, the reaction mixture was concentrated until dryness. For further processing the copper complex was suspended in 80 ml dichloromethane and 70 ml 10% sulfuric acid were added. After strong stirring the phases were separated and the aqueous phase was extracted two times with 50 ml dichloromethane. The combined organic phases were dried over sodium sulfate and concentrated in a rotary evaporator until dryness. The residue was recrystallized in diethyl ether/petroleum ether. The crystalline product was filtered and dried under vacuum. The yield of $N^1$-(2-methoxyethyl)-$N^4$,$N^4$-dimethyl-2-oxobutaneamide was 5.96 g (60%).

IR (in substance, cm$^{-1}$): 3372, 3311, 3202, 2974, 2934, 2879, 2830, 1787, 1741, 1674, 1634, 1530, 1495, 1473, 1439, 1400, 1358, 1267, 1193, 1176, 1158, 1124, 1107, 1064, 1016, 960, 901, 825, 815, 767, 715.

Enol form
$^1$H-NMR (DMSO-d$_6$, 400 MHz): δ [ppm]=3.0 (6H), 3.2 (3H), 3.3-3.4 (4H), 6.1 (1 H), 8.2 (1 H), 15.5 (1 H).

Q. Ethyl-N-[4-(dimethylamino)-2,4-dioxobutanoyl]-N-methylglycinate

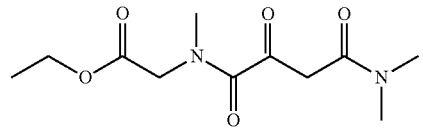 [SMILES: CCOC(=O)CN(C)C(=O)C(=O)CC(=O)N(C)C]

4.73 g (58.0 mmol) dimethylamine hydrochloride were suspended in 100 ml dichloromethane and 11.1 g (58.0 mmol) (2Z)-(2,2-dimethyl-5-oxo-1,3-dioxolane-4-yliden)acetyl chloride (prepared according to J. Banville et al, *Tetrahedron Letters*, 2010, 51, 3170-3173) dissolved in 100 ml dichloromethane were added dropwise. Stirring was carried out at room temperature over night, subsequently 11.7 g (116 mmol) triethylamine were added followed by boiling under reflux for two hours. The suspension was filtered and the filtrate concentrated until dryness. The residue was collected in 170 ml ethyl acetate, filtered and again concentrated until dryness. 11 g (55%) (2Z)-2-(2,2-dimethyl-5-oxo-1,3-dioxolane-4-yliden)-N,N-dimethylacetamide were added.

$^1$H-NMR (DMSO-d$_6$, 400 MHz): δ [ppm]=1.7 (6H), 2.9 (3H), 3.0 (3H), 6.0 (1 H).

15.4 (100 mmol) sarcosine ethylester hydrochloride and 10.1 g (100 mmol) triethylamine were suspended in 100 ml dichloromethane. 5.0 g (25 mmol) (2Z)-2-(2,2-dimethyl-5-oxo-1,3-dioxolane-4-yliden)-N,N-dimethylacetamide were added followed by boiling under reflux for one hour. The reaction mixture was concentrated until dryness and the residue collected in 20 ml ethyl acetate. After filtering the filtrate was concentrated until dryness. The raw product was purified using column chromatography (silica gel, ethyl acetate). The yield of ethyl-N-[4-(dimethylamino)-2,4-dioxobutanoyl]-N-methylglycinate was 2.7 g (42%).

IR (in substance, cm$^{-1}$): 3351, 2982, 2939, 1729, 1682, 1634, 1508, 1397, 1375, 1353, 1257, 1198, 1096, 1021, 982, 916, 864, 822, 771.

Keto form:
$^1$H-NMR (DMSO-d$_6$, 400 MHz): δ [ppm]=1.2 (3H), 2.8-3.1 (9H), 3.8-4.0 (2H), 4.1 (2H), 4.1-4.3 (2H).

R. $N^1$-[2-(Dimethylamino)-2-oxoethyl]-$N^1$,$N^4$,$N^4$-trimethyl-2-oxobutanediamide

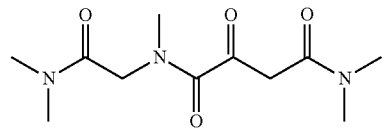

4.73 g (58.0 mmol) dimethylamine hydrochloride were suspended in 100 ml dichloromethane and 11.1 g (58.0 mmol) (2Z)-(2,2-dimethyl-5-oxo-1,3-dioxolane-4-yliden) acetyl chloride (prepared according to J. Banville et al, *Tetrahedron Letters*, 2010, 51, 3170-3173) dissolved in 100 ml dichloromethane were added dropwise. Stirring was carried out at room temperature over night, subsequently 11.7 g (116 mmol) triethylamine were added followed by boiling under reflux for two hours. The suspension was filtered and the filtrate concentrated until dryness. The residue was collected in 170 ml ethyl acetate, filtered and again concentrated until dryness. 11 g (55%) (2Z)-2-(2,2-dimethyl-5-oxo-1,3-dioxolane-4-yliden)-N,N-dimethylacetamide were obtained.

$^1$H-NMR (DMSO-$d_6$, 400 MHz): δ [ppm]=1.7 (6H), 2.9 (3H), 3.0 (3H), 6.0 (1 H).

3.83 g (25.1 mmol) N,N-dimethyl-2-(methylamino)acetamide hydrochloride (Sigma-Aldrich: CDS007544) and 2.79 g (27.6 mmol) triethylamine were suspended in 8 ml ethanol. 1.00 g (5.02 mmol) (2Z)-2-(2,2-dimethyl-5-oxo-1,3-dioxolane-4-yliden)-N,N-dimethylacetamide were added and stirred at room temperature for 30 minutes. 5 ml 6N HCl-solution were added and the reaction mixture was concentrated until dryness. The residue was collected in 10 ml water and 20 ml ethyl acetate. The phases were separated and the aqueous phase was extracted with ethyl acetate twice. The organic phases were dried over sodium sulfate and concentrated until dryness. The raw product was purified using column chromatography (silica gel, dichloromethane/ethanol). The yield of N$^1$-[2-(dimethylamino)-2-oxoethyl]-N$^1$,N$^4$,N$^4$-trimethyl-2-oxobutanediamide was 0.94 g (77%).

IR (in substance, cm$^{-1}$): 3487, 2935, 1780, 1721, 1632, 1492, 1397, 1354, 1335, 1305, 1259, 1144, 1095, 1054, 981, 942, 857, 813, 760.

Keto form:
$^1$H-NMR (DMSO-$d_6$, 400 MHz): δ [ppm]=2.9-3.1 (15H), 3.9 (2H), 4.1-4.3 (2H).

S. Ethyl-N-[4-(dimethylamino)-2,4-dioxobutanoyl]glycinate

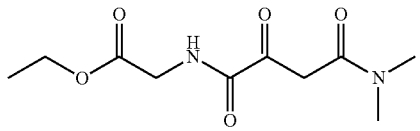 [SMILES: CCOC(=O)CNC(=O)C(=O)CC(=O)N(C)C]

53.30 g (0.475 mol) sodium tert-butoxide were suspended in 300 ml diethyl ether. 73.07 g (0.500 mol) diethyl oxalate were added under cooling in an ice bath. Stirring was carried out for 30 min under cooling, 43.57 g (0.500 mol) N,N-dimethylacetamide were added and the reaction mixture was stirred for 2 h. For further processing filtering was carried out and the solid was disintegrated in 260 ml 4N hydrochloric acid and 750 ml ethyl acetate. After separation of the phases the aqueous phase was extracted with 300 ml ethyl acetate twice. The combined organic phases were dried over sodium sulfate and concentrated in a rotary evaporator until dryness. The yield of ethyl 4-(dimethylamino)-2,4-dioxobutanoate was 54.3 g (58%).

$^1$H-NMR (CDCl3, 400 MHz): δ [ppm]=1.38 (3H), 3.06 (6H), 4.33 (2H), 6.25 (1 H)

32.56 g (163.1 mmol) copper acetate monohydrate were suspended in 470 ml ethanol and heated up to 75° C. 61.06 g (326.2 mmol) ethyl 4-(dimethylamino)-2,4-dioxobutanoate were added in one portion. The mixture was stirred for 40 min at 75° C. The copper complex was precipitated at 4° C.

7.0 g (68 mmol) glycine ethyl ester (prepared according to E. Fischer, *Chemische Berichte*, 1906, vol. 39, p. 541) were dissolved in 13 ml ethanol, 1.0 g (2.3 mmol) of the copper complex were added and stirred at room temperature for one hour. Subsequently, the reaction mixture was concentrated until dryness. For further processing the copper complex was suspended in 80 ml dichloromethane and 50 ml 10% sulfuric acid were added. After strong stirring the phases were separated and the aqueous phase was extracted with 50 ml dichloromethane twice. The combined organic phases were dried over sodium sulfate and concentrated in a rotary evaporator until dryness. The raw product was purified using column chromatography (silica gel, ethyl acetate/petroleum ether). The yield of ethyl-N-[4-(dimethylamino)-2,4-dioxobutanoyl]glycinate was 0.5 g (45%).

IR (in substance, cm$^{-1}$): 3389, 2983, 2942, 2324, 2083, 1982, 1739, 1678, 1631, 1608, 1520, 1404, 1354, 1278, 1255, 1179, 1144, 1097, 1084, 1065, 1023, 973, 915, 860, 819, 773, 717.

Enol form
$^1$H-NMR (DMSO-$d_6$, 400 MHz): δ [ppm]=1.2 (3H), 3.0 (6H), 3.9 (2H), 4.1 (2H), 6.2 (1H), 8.7 (1 H), 15.5 (1 H).

T. N$^1$-(2-Methoxyethyl)-N$^1$,N$^4$,N$^4$-trimethyl-2-oxobutanediamide

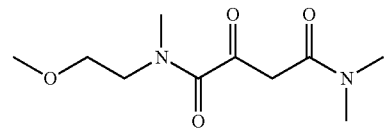

19.5 g (219 mmol) N-(2-methoxyethyl)methylamine and 22.2 g (219 mmol) triethylamine were dissolved in 400 ml diethyl ether and cooled in an ice bath. 30.0 g (219 mmol) ethyl chlorooxoacetate was added dropwise and the reaction mixture was left to warm up to room temperature. The suspension was filtered and the filtrate concentrated until dryness. 36.9 g ethyl-[(2-methoxyethyl)(methyl)amino](oxo)acetate in the form of a yellow oil were obtained, which was used for further processing without further purification.

20.8 g (185 mmol) sodium tert-butoxide were suspended in 200 ml diethyl ether. 36.9 g (195 mmol) ethyl-[(2-methoxyethyl)(methyl)amino](oxo) acetate were added under cooling in an ice bath. Stirring was carried out for 30 min at room temperature, 17.0 g (195 mmol) N,N-dimethylacetamide were added and the reaction mixture was stirred at room temperature for two hours. 123 ml 6N hydrochloric acid, 130 ml ethyl acetate and 30 ml water were added to the reaction mixture. After separation of the phases the aqueous phase was extracted with 100 ml ethyl acetate three times. The combined organic phases were dried over sodium sulfate and concentrated in a rotary evaporator until dryness. The raw product was purified using column chromatography (silica gel, dichloromethane/acetone). The yield of N$^1$-(2-methoxyethyl)-N$^1$,N$^4$,N$^4$-trimethyl-2-oxobutanediamide was 4.5 g (10%).

IR (in substance, cm$^{-1}$): 3482, 2935, 1720, 1631, 1492, 1454, 1401, 1355, 1293, 1260, 1198, 1115, 1069, 1014, 972, 828, 772721.

Keto form
$^1$H-NMR (DMSO-$d_6$, 400 MHz): δ [ppm]=2.8-3.0 (9H), 3.3 (3H), 3.4-3.5 (4H), 3.9 (2H).

U. $N^4$-(2-Hydroxyethyl)-$N^1$,$N^1$,$N^4$-trimethyl-2-oxobutanediamide

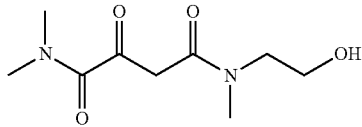

1.18 g (15.7 mmol) 2-(methylamino)ethanol were dissolved in 50 ml dichloromethane and 2.39 g (23.6 mmol) triethylamine were added. 3.00 g (15.7 mmol) (2Z)-(2,2-dimethyl-5-oxo-1,3-dioxolane-4-yliden)acetyl chloride (prepared according to J. Banville et al, Tetrahedron Letters, 2010, 51, 3170-3173) were added and stirred at room temperature for 30 minutes. Subsequently, boiling under reflux for four hours followed. The reaction mixture was concentrated until dryness and the residue was collected in 300 ml ethyl acetate. The suspension was filtered and the filtrate concentrated until dryness. The residue was purified using column chromatography (silica gel, dichloromethane/ethanol). 1.5 g (42%) (2Z)-2-(2,2-dimethyl-5-oxo-1,3-dioxolane-4-yliden)-N-(2-hydroxyethyl)-N-methylacetamide were obtained.

$^1$H-NMR (DMSO-$d_6$, 400 MHz): δ [ppm]=1.7 (6H), 3.0 (3H), 3.4-3.6 (4H), 4.7-4.9 (1 H), 6.0-6.2 (1 H).

1.0 g (4.4 mmol) (2Z)-2-(2,2-dimethyl-5-oxo-1,3-dioxolane-4-yliden)-N-(2-hydroxyethyl)-N-methylacetamide were dissolved in 8 ml ethanolic dimethylamine solution (33%) and stirred for 15 minutes at room temperature. Concentration until dryness followed and 0.95 g (99%) $N^4$-(2-hydroxyethyl)-$N^1$,$N^1$,$N^4$-trimethyl-2-oxobutanediamide were obtained.

IR (in substance, cm$^{-1}$): 3401, 2935, 1720, 1626, 1490, 1448, 1401, 1359, 1297, 1261, 1208, 1110, 1074, 1047, 950, 880, 863, 806, 773, 719.

Keto form:

$^1$H-NMR (DMSO-$d_6$, 400 MHz): δ [ppm]=2.8-3.1 (9H), 3.3-3.5 (4H), 3.9-4.0 (2H), 4.9 (1 H).

Testing Method:

The excellent Fe utilizations that can be accomplished through the Fe complexes according to the invention were measured by means of the following mouse model.

(In each case 6 animals per substance were used. There was a negative group (water) with 6 animals and as a positive group $FeSO_4$ was used with 6 animals, too).

Male NMRI (SPF) mice (approximately 3 weeks old) were fed a low-iron diet (approx. 5 ppm iron) for approximately 3 weeks. The iron complexes were then administered to them by means of a stomach tube (2 mg iron/kg body weight/day) for 2 times 5 days, with an interruption of 2 days (days 1-5 and 8-12). Utilization on day 15 was calculated from the hemoglobin increase and the body weight increase in accordance with the formula $$\text{Utilization (\%)} = \frac{\Delta \text{ iron utilization} * 100}{\text{Fe Dos.}} = \frac{(\text{Fe ut.} - \text{Fe ut. Control}) * 100}{\text{Fe Dos.}}$$

$= [(Hb_{2(3)}*BW_{9(14)}-Hb_1*BW_4)*0.07*0.0034-(Hb_{2(3)Control}*BW_{9(14)Control}-Hb_{1Control}*BW_{4Control})*0.07*0.0034)]*100/\text{Fe Dos.}$ $= [(Hb_{2(3)}*BW_{9(14)}-Hb_1*BW_4)*0.000238-(Hb_{2(3)Control}*BW_{9(14)Control}-Hb_{1Control}*BW_{4Control})*0.000238]*100/\text{Fe Dos.}$ $= [(Hb_{2(3)}*BW_{9(14)}-Hb_1*BW_4-Hb_{2(3)Control}*BW_{9(14)Control}+Hb_{1Control}*BW_{4Control})*0.0238/\text{Fe Dos.}$ 0.07=Factor for 70 ml blood per kg body weight (BW)
0.0034=Factor for 0.0034 g Fe/g Hb
$Hb_1$=Hemoglobin level (g/l) on day 1
$Hb_{2(3)}$=Hemoglobin level (g/l) on day 8 (or 15)
$BW_4$=body weight (g) on day 1
$BW_{9(14)}$=body weight (g) on day 8 (or 15)
$Hb_{1\ Control}$=average hemoglobin level (g/l) on day 1 in the control group,
$Hb_{2(3)\ Control}$=average hemoglobin level (g/l) on day 8 (or 15) in the control group,
$BW_{4\ Control}$=average body weight (g) on day 1 in the control group,
$BW_{9(14)\ Control}$=average body weight (g) on day 8 (or 15) in the control group,
Fe Dos.=entire administered iron (mg Fe) over 5 or 10 days,
Fe ut.=$(Hb_{2(3)}*BW_{9(14)}-Hb_1*BW_4)*0.07*0.0034$ (mg Fe)
Δ Utilization=Fe tot. utilized (examined group)−Fe ut. Control group, utilized from food, (mg Fe)

The following Table 1 shows the iron utilization of the compound of Example 1 and compares it with the corresponding value obtained for the compound of Example 32 of WO11117225A1:

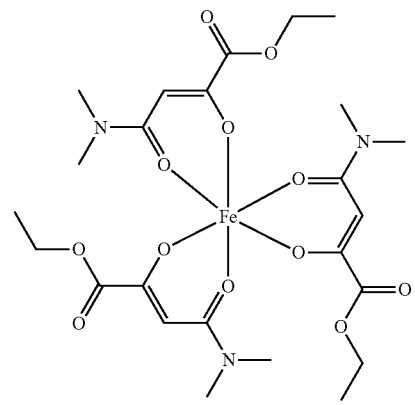

TABLE 1
| Example-No. | Utilization n 15 d (abs. %) |
|---|---|
| 1 | 98 |
| 2 | 75 |
| 4 | 92 |
| 5 | 82 |
| 7 | 68 |
| 11 | 50 |
| 12 | 80 |
| 13 | 70 |
| 16 | 65 |
| 17 | 91 |
TABLE 1-continued
| Example-No. | Utilization n 15 d (abs. %) |
|---|---|
| 18 | 78 |
| 21 | 86 |
| Comparative Example (Example 32 of WO11117225A1) | 81 |
The table below shows that the structural change compared to WO11117225A1 generally leads to improved iron utilization:
| Example according to the invention | Example from WO11117225A1 |
|---|---|
| Example 2 | Example 62 |
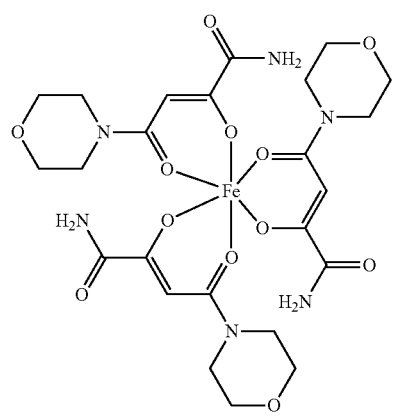
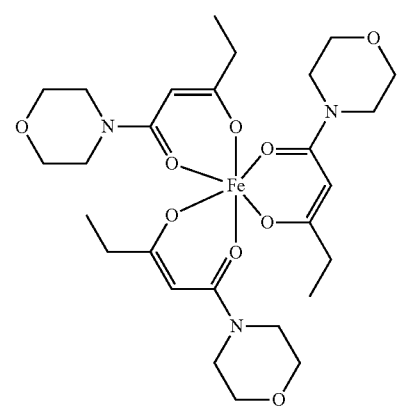
| 75% | 68% |
|---|---|
| Example 1 | Example 32 |
|---|---|
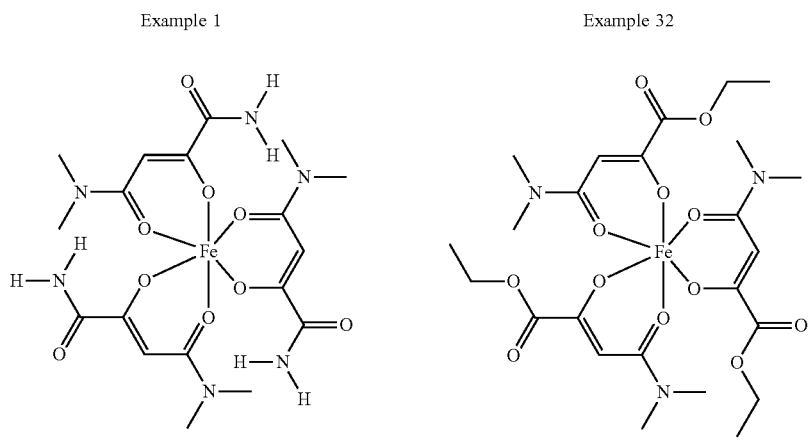
| 98% | 81% |
|---|---|

-continued
| Example according to the invention | Example from WO11117225A1 |
|---|---|
| Example 1 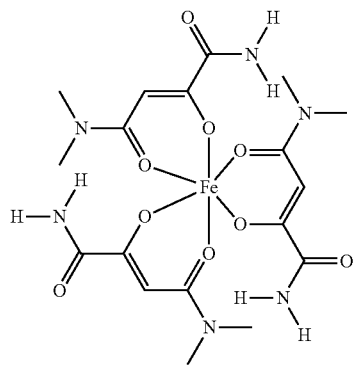 98% | Example 19 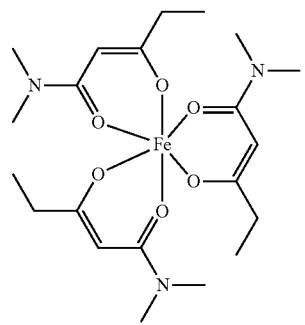 73% |
| Example 5 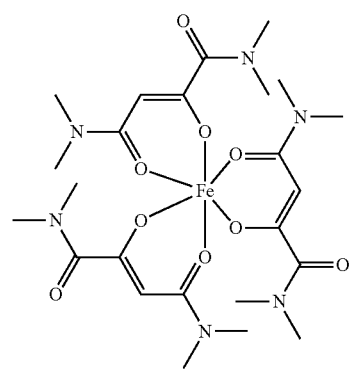 82% | Example 19 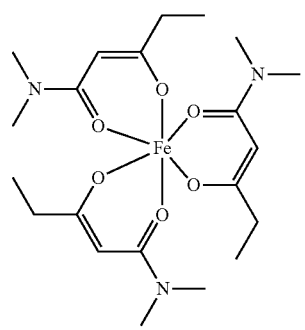 73% |
| Example 21 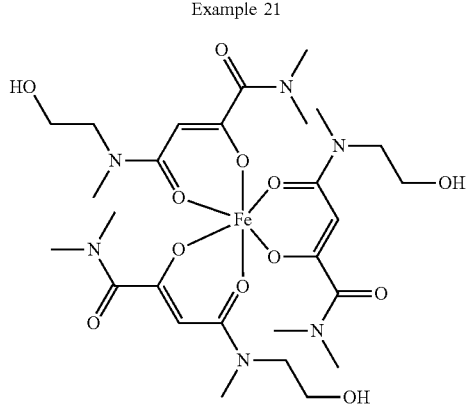 86 % | Example 42 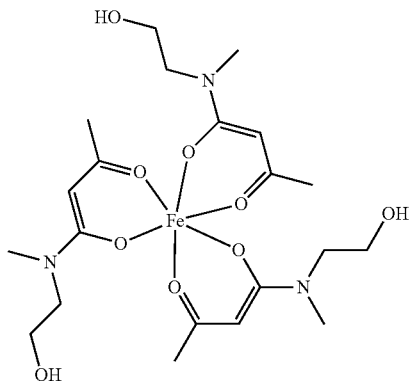 30% |

The measured iron utilization values represent an important parameter with regard to the indication of treatment of iron deficiency and iron deficiency anemia, because this parameter reflects not only the absorption of iron, but also the relationship between body weight and iron intake, which is particularly important when using growing animals in the animal model. If only the hemoglobin values are considered, which represent a value for the truly absorbed and used iron, the part resulting from the growth of the animals would remain unconsidered. Thus, the iron utilization is a more accurate measure, although iron utilization and hemoglobin levels usually correlate with each other. A consideration of the pure iron serum levels, which would also be measurable, is less useful because, although an indication of the amount of iron which gets into the body is made, no indication can be made about the amount which can be used by the body.

The test results demonstrate that the iron complex compounds of the invention have excellent iron utilization so that they are useful as agents for the treatment of iron deficiency anemia and associated symptoms.

The test results further demonstrate that the compound according to Example 1 of the present application exhibits a significantly improved iron utilization compared to Example 32 of WO11117225A1.

Comparison of the pH-Dependent Solubility:

For this purpose, a certain amount of iron (III) complex (sample weight) to be examined, generally in the concentration rage of 0.4-0.8 mg/ml, based on the amount of iron in the iron complex, was placed in an aqueous medium (water) with adjusted pH value (pH 6.5) and stirred for the indicated time (4 h) at 25° C. The pH was adjusted to 6.5 with a phthalate buffer (0.1 m). Subsequently, the iron content of the solution in mg/ml, based on iron, was determined photometrically (cuvettes: single-use cuvettes 1 cm Plastibrand PS 2.5 ml ISO cert. 9001 14001; device: UV device type SPECORD 205 manufacturer Jena Analytik). This value represents the solubility of the iron complex. If the weighed amount of the iron complex was completely dissolved, the measured value was indicated by the prefix ">". The results are shown in Table 2 below. It shows that the compounds according to the present invention exhibit significantly higher solubility than the compound of Example 32 of WO11117225A1.

The iron (III) complex compounds according to the invention preferably have a solubility in water at 25° C. at pH 6.5 of at least 0.3 mg/ml based on the iron, which is determined photometrically as described above. Preferred iron (III) complex compounds have a solubility in water at 25° C. at pH 6.5 of at least 0.4 mg/ml based on the iron. Especially preferred iron (III) complex compounds have a solubility in water at 25° C. at pH 6.5 of at least 0.5 mg/ml based on the iron.

Good water solubility of the iron(III) complex compounds is a prerequisite for an improved oral absorption. Oral medications, which have better solubility, generally lead to a better iron uptake. Water-insoluble compounds may, in general, not be used for oral administration, since practically no absorption takes place.

TABLE 2

Comparison of the pH-dependent solubility:

| Example | Fe content % | pH | time | sample weight mg | mg/ml Fe | dissolved? | color filtered | Intensity | Volume Aliquot in ml | Absorption at 515 nm | Solubility based on amount of iron in mg/ml |
|---|---|---|---|---|---|---|---|---|---|---|---|
| Comparative Example (Example 32 of WO11117225A1) | 9.43 | 6.5 | 4 h | 6.7 | 0.75 | no | red | +++ | 0.1 | 0.3764 | 0.206 |
| Example 1 | 11.28 | 6.5 | 4 h | 5.5 | 0.61 | yes | red | +++ | 0.1 | 0.9643 | 0.529 |
| Example 5 | 8.43 | 6.5 | 4 h | 7.5 | 0.53 | yes | red | +++ | 0.1 | 1.1340 | >0.55 |
| Example 11 | 7.88 | 6.5 | 4 h | 7.7 | 0.51 | yes | orange | +++ | 0.1 | 0.6783 | >0.33 |
| Example 12 | 6.20 | 6.5 | 4 h | 9.5 | 0.49 | yes | orange | +++ | 0.1 | 1.0464 | >0.51 |
| Example 13 | 6.02 | 6.5 | 4 h | 9.8 | 0.49 | yes | orange | +++ | 0.1 | 1.0656 | >0.52 |
| Example 16 | 7.21 | 6.5 | 4 h | 8.2 | 0.49 | no | orange | +++ | 0.1 | 0.9226 | 0.45 |
| Example 17 | 6.64 | 6.5 | 4 h | 9.2 | 0.51 | no | orange | +++ | 0.1 | 0.9607 | 0.47 |
| Example 18 | 5.05 | 6.5 | 4 h | 12.0 | 0.51 | no | orange | +++ | 0.1 | 1.2031 | 0.58 |
| Example 21 | 7.34 | 6.5 | 4 h | 7.0 | 0.43 | no | orange | +++ | 0.1 | 1.0239 | 0.49 |

PREPARATION EXAMPLES

Example 1

Tris-($N^4,N^4$-dimethyl-2-oxobutanediamide)-iron (III)-complex

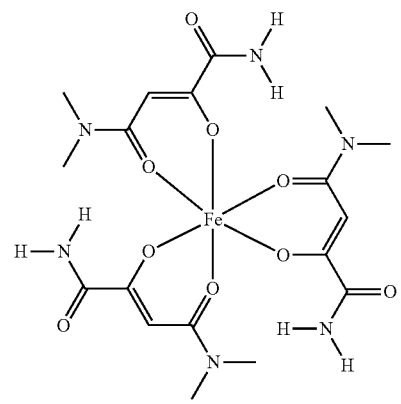

1.75 g (8.78 mmol) iron(III)acetate was dissolved in 160 ml 94% ethanol and 5.01 g (31.6 mmol) $N^4,N^4$-dimethyl-2-oxobutanediamide were added and boiled for 1 hour under reflux. The resulting iron complex was precipitated 4° C.

The precipitated iron complex was filtered and dried under vacuum at 50° C. for one day. 3.74 g (81% yield) product as red solid were achieved.

IR (in substance, cm$^{-1}$): 3437, 3405, 3153, 2931, 2323, 1680, 1594, 1567, 1498, 1403, 1352, 1258, 1171, 1142, 1058, 1001, 936, 814, 766, 735, 686.

Elemental analysis: C, 41.17%; H, 5.2%; N, 15.9%.

Fe content: 10.3% [m/m].

2. Tris-(4-(morpholine-4-yl)-2,4-dioxobutaneamide)-iron(III)-complex

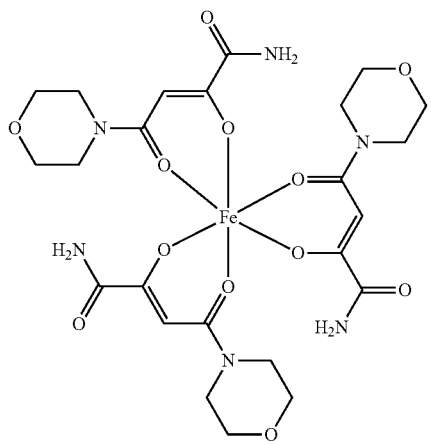

0.60 g (3.1 mmol) iron(III) acetate were dissolved in 150 ml 94% ethanol and 2.00 g (10.0 mmol) 4-(morpholine-4-yl)-2,4-dioxobutaneamide were added. Boiling was carried out under reflux. After addition of seed crystals the final iron complex was precipitated at 4° C. and filtered off. The product was dried for one day at 50° C. under fine vacuum. 1.1 g (54% yield) product in the form of a red solid were obtained.

IR (in substance, cm$^{-1}$): 3608, 3352, 3135, 2960, 2918, 2850, 2324, 2050, 1981, 1685, 1570, 1498, 1460, 1443, 1373, 1301, 1273, 1245, 1145, 1112, 1050, 1017, 986, 936, 850, 817, 764, 737, 676.

Elemental analysis: C, 42.71%; H, 5.7%; N, 11.94%.

Fe content: 8.3% [m/m].

3. Tris-(N$^4$,N$^4$-diethyl-2-oxobutanediamide)-iron(III)-complex

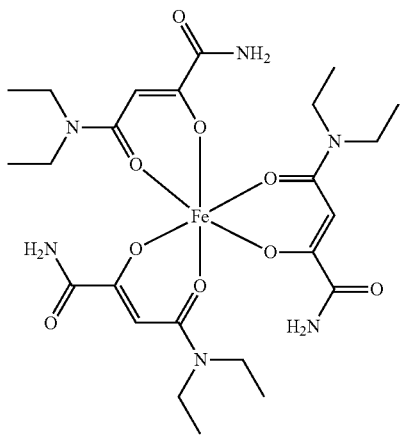

0.13 g (0.83 mmol) iron(III) chloride were dissolved in 10 ml water and 0.50 g (2.5 mmol) N$^4$,N$^4$-diethyl-2-oxobutanediamide were added. Stirring was carried out for 15 minutes at room temperature and subsequently the reaction mixture was cooled in an ice bath. 0.45 g (3.3 mmol) sodium acetate trihydrate were added followed by stirring for further 15 min in the ice bath. The precipitated iron complex was filtered off and dried over night at 50° C. under fine vacuum. 0.5 g (92% yield) product in the form of orange solid were obtained solid.

IR (in substance, cm$^{-1}$): 3458, 3301, 2975, 2935, 1681, 1618, 1566, 1496, 1453, 1437, 1376, 1355, 1307, 1270, 1215, 1160, 1078, 1035, 964, 925, 818, 771, 743, 659.

Elemental analysis: C, 46.31%; H, 6.5%; N, 13.56%.

Fe content: 9.1% [m/m].

4. Tris-(2,4-dioxo-4-(pyrrolidine-1-yl)butaneamide)-iron(III)-complex

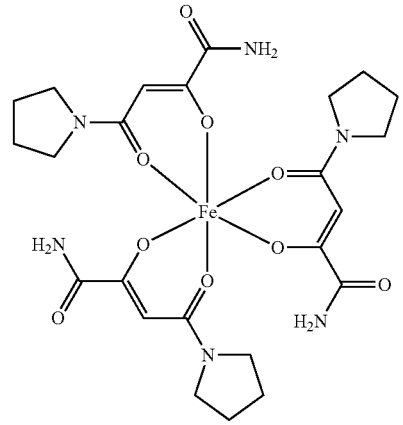

0.28 g (1.4 mmol) iron(III) acetate were suspended in 10 ml ethyl acetate and 0.80 g (4.3 mmol) 2,4-dioxo-4-(pyrrolidine-1-yl)butaneamide were added. The reaction mixture was heated up to 50° C. Subsequently, 30 ml ethyl acetate and 20 ml ethanol were added and the suspension heated up to 90° C. Subsequently, the reaction mixture was cooled in an ice bath. The precipitated complex was filtered off and dried for three days The precipitated complex was filtered off and dried at 50° C. under fine vacuum. 0.67 g (62% yield) product in the form of red solid were obtained.

IR (in substance, cm$^{-1}$): 3454, 3367, 3178, 2968, 2877, 1685, 1627, 1560, 1493, 1474, 1457, 1367, 1254, 1225, 1182, 1134, 1116, 1059, 1026, 972, 938, 916, 856, 814, 769, 717, 659.

Elemental analysis: C, 47.45%; H, 5.6%; N, 13.32%.

Fe content: 8.8% [m/m].

5. Tris-(N,N,N',N'-tetramethyl-2-oxobutanediamide)-iron(III)-complex

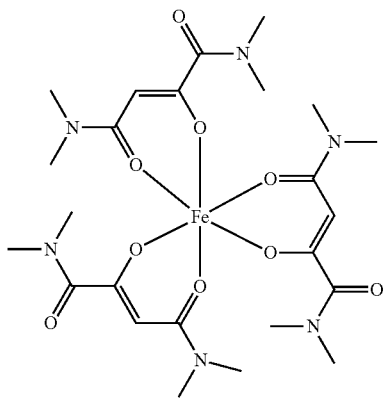

0.54 g (3.3 mmol) iron(III) chloride were dissolved in 20 ml water and 2.0 g (10 mmol) N,N,N',N'-tetramethyl-2-oxobutanediamide were added. Stirring was carried out for 15 minutes at room temperature and subsequently the reaction mixture was cooled in an ice bath. 1.8 g (13 mmol) sodium acetate trihydrate were added and stirred for further 10 min in the ice bath. The aqueous reaction mixture was extracted with 50 ml chloroform three times. The combined organic phases were concentrated at the rotary evaporator until dryness and evaporated with 50 ml toluene two more times. The iron complex was dried at 50° C. over night under fine vacuum. 1.6 g (73% yield) product in the form of red solid.

IR (in substance, cm$^{-1}$): 3496, 2929, 1634, 1568, 1486, 1392, 1354, 1259, 1203, 1174, 1118, 1059, 1006, 962, 900, 811, 771, 710, 665.

Elemental analysis: C, 45.95%; H, 6.4%; N, 13.19%.
Fe content: 9.1% [m/m].

6. Tris-(4-(4-hydroxypiperidine-1-yl)-2,4-dioxobutaneamide)-iron(III)-complex

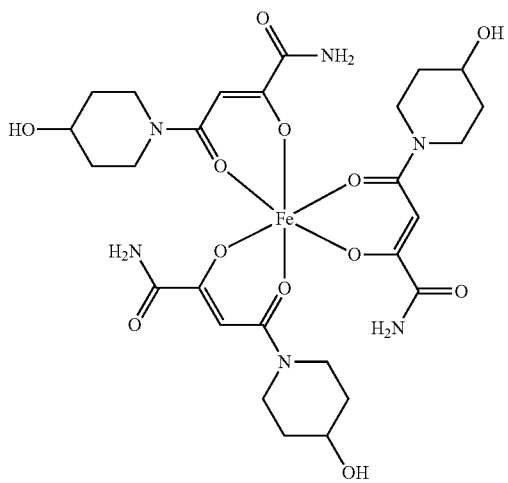

144 mg (0.734 mmol) iron(III) acetate were suspended in 50 ml ethanol and 471 mg (2.20 mmol) 4-(4-hydroxypiperidine-1-yl)-2,4-dioxobutaneamide were added. The reaction mixture was boiled under reflux for one hour. 60 ml toluene were added and concentrated until dryness. The residue was collected in an ethanol/toluene-mixture (40 ml/60 ml) two more times and concentrated until dryness. The residue was dried at 50° C. under fine vacuum. 0.5 g (98% yield) product in the form of red solid were obtained.

IR (in substance, cm$^{-1}$): 3445, 3298, 2946, 2924, 2324, 2051, 1981, 1687, 1666, 1598, 1561, 1493, 1448, 1370, 1262, 1227, 1138, 1075, 1050, 1023, 985, 928, 834, 816, 767, 664.

Elemental analysis: C, 46.26%; H, 5.8%; N, 11.60%.
Fe content: 7.7% [m/m].

7. Tris-(N$^1$,N$^4$,N$^4$-trimethyl-2-oxobutanediamide)-iron(III)-complex

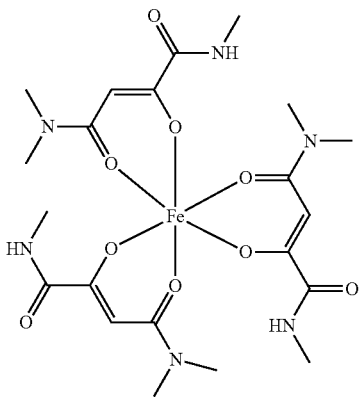

0.784 g (4.83 mmol) iron(III) chloride were dissolved in 20 ml water and 2.55 g (14.5 mmol) N',N$^4$,N$^4$-trimethyl-2-oxobutanediamide were added. Stirring was carried out for 15 minutes at room temperature, followed by cooling of the reaction mixture in an ice bath. 2.16 g (19.2 mmol) sodium acetate trihydrate were added and stirred for 15 min in the ice bath. The precipitated complex was filtered off and dried at 50° C. over night under fine vacuum. 1.5 g (53% yield) product in the form of orange solid were obtained.

IR (in substance, cm$^{-1}$): 3352, 2934, 2877, 2324, 1674, 1598, 1566, 1504, 1405, 1356, 1253, 1176, 1152, 1063, 992, 980, 961, 930, 896, 847, 813, 769, 748, 736, 706.

Elemental analysis: C, 43.74%; H, 5.9%; N, 14.53%.
Fe content: 9.5% [m/m].

8. Tris-(N,N'-Dimethyl-2-oxobutanediamide)-iron(III)-complex

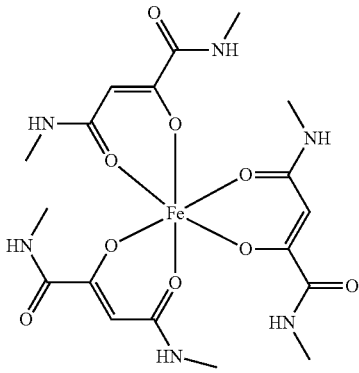

242 mg (1.49 mmol) iron(III) chloride were dissolved in 10 ml water and 707 mg (4.47 mmol) N,N'-dimethyl-2-oxobutanediamide were added. Stirring was carried out for 15 minutes at room temperature. 812 mg (5.97 mmol) sodium acetate trihydrate were added and stirred for further 30 min. The precipitated iron complex was filtered off and dried at 50° C. for 4 days under fine vacuum. 587 mg (74% yield) product in the form of orange solid were obtained.

IR (in substance, cm$^{-1}$): 3334, 3256, 3129, 2940, 1673, 1603, 1546, 1507, 1407, 1278, 1239, 1160, 1139, 1087, 1028, 963, 897, 817, 800, 777, 724, 691.

Elemental analysis: C, 40.04%; H, 5.1%; N, 15.49%.

Fe content: 10.2% [m/m].

9. Tris-($N^1,N^1,N^4$-Trimethyl-2-oxobutanediamide)-iron(III)-complex

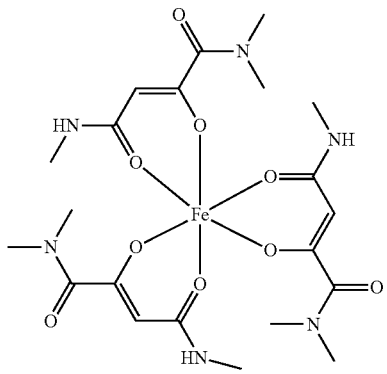

75 mg (0.46 mmol) iron(III) chloride were dissolved in 3 ml water and 239 mg (1.39 mmol) $N^1,N^1,N^4$-trimethyl-2-oxobutanediamide were added. Stirring was carried out for 15 minutes at room temperature, 252 mg (1.85 mmol) sodium acetate trihydrate were added and stirred for further 30 min. The reaction (mixture was concentrated until dryness and the residue was collected in 20 ml chloroform. The insoluble parts were filtered off and the filtrate concentrated until dryness. Drying was carried out at 50° C. over night under fine vacuum. 230 mg product a purity of 78% were obtained.

IR (in substance, cm$^{-1}$): 3270, 3118, 2932, 2051, 1578, 1491, 1433, 1395, 1278, 1192, 1157, 1123, 1076, 966, 902, 778.

Elemental analysis: C, 41.89%; H, 6.1%; N, 11.20%.

Fe content: 7.7% [m/m].

10. Tris-($N^4,N^4$-Diethyl-$N^1,N^1$-dimethyl-2-oxobutanediamide)-iron(III)-complex

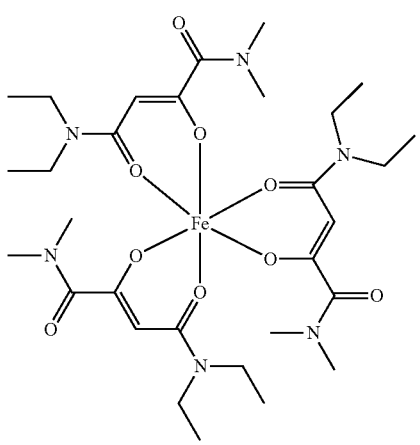

0.49 g (3.0 mmol) iron(III) chloride were dissolved in 20 ml water and 2.0 g (9.0 m mol) $N^4,N^4$-diethyl-$N^1,N^1$-dimethyl-2-oxobutanediamide were added. Stirring was carried out for 15 minutes at room temperature followed by cooling of the reaction mixture in an ice bath. 1.63 g (11.8 mmol) sodium acetate trihydrate were added and stirred for 30 min. The reaction mixture was extracted with 50 ml chloroform three times, dried over sodium sulfate and concentrated until dryness. The residue was stripped with 50 ml toluene three times to remove acetic acid. The residue was dried at 50° C. over night under fine vacuum and 1.8 g (83%) product in the form of a wine red solid were obtained.

IR (in substance, cm$^{-1}$): 3481, 2973, 2933, 2050, 1636, 1602, 1563, 1511, 1487, 1435, 1392, 1376, 1357, 1308, 1274, 1218, 1198, 1160, 1120, 1080, 1036, 964, 929, 887, 808, 789, 767, 707.

Elemental analysis: C, 51.12%; H, 7.2%; N, 11.68%.

Fe content: 8.0% [m/m].

11. Tris-(N,N-Dimethyl-3,4-dioxo-4-(pyrrolidine-1-yl)butaneamide)-iron(III) complex

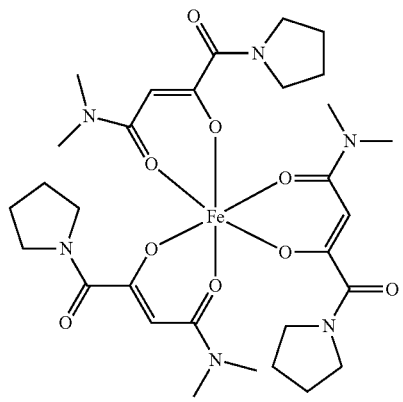

0.48 g (3.0 mmol) iron(III) chloride were dissolved in 20 ml water and 2.0 g (8.9 mmol) N,N-dimethyl-3,4-dioxo-4-(pyrrolidine-1-yl)butaneamide were added. Stirring was carried out for 15 minutes at room temperature followed bcooling of the reaction mixture in an ice bath. 1.61 g (11.8 mmol) sodium acetate trihydrate were added and stirred for further 30 min. The reaction mixture was extracted with 50 ml chloroform three times, dried over sodium sulfate and concentrated until dryness. The residue was stripped with 50 ml toluene three times. The residue was dried at 50° C. over night under fine vacuum and 2.1 g (97%) product in the form of a wine red solid were obtained.

IR (in substance, cm$^{-1}$): 3465, 2949, 2875, 2324, 2051, 1694, 1605, 1563, 1504, 1402, 1357, 1294, 1255, 1225, 1162, 1061, 1012, 980, 960, 920, 896, 850, 809, 762, 705.

Elemental analysis: C, 51.51%; H, 6.4%; N, 11.73%.

Fe content: 8.1% [m/m]. y

12. Tris-(N⁴-[2-(dimethylamino)-2-oxoethyl]-N¹,N¹,N⁴-trimethyl-2-oxobutanediamide)-iron(III)-complex

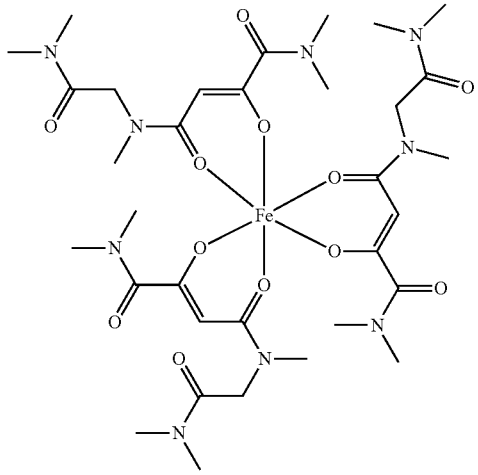

0.40 g (2.5 mmol) iron(III) chloride were dissolved in 20 ml water and 2.0 g (7.5 mmol) N⁴-[2-(dimethylamino)-2-oxoethyl]-N¹,N¹,N⁴-trimethyl-2-oxobutanediamide dissolved in 3 ml ethanol were added. Stirring was carried out for 15 minutes at room temperature, 1.4 g (9.9 mmol) sodium acetate trihydrate were added and stirred for further 30 min. The reaction mixture was extracted with 50 ml chloroform three times, dried over sodium sulfate and concentrated until dryness. The residue was stripped with 50 ml toluene two times. Drying was carried out at 50° C. over night under fine vacuum and 2.1 g (98%) product in the form of a red solid were obtained.

IR (in substance, cm⁻¹): 3453, 2933, 2324, 2164, 2051, 1981, 1628, 1566, 1510, 1485, 1395, 1364, 1335, 1298, 1254, 1218, 1143, 1112, 1060, 1039, 964, 905, 825, 808, 763, 713, 668.

Elemental analysis: C, 46.06%; H, 6.8%; N, 14.46%.

Fe content: 6.2% [m/m].

13. Tris-(N⁴-(2-methoxyethyl)-N¹,N¹,N⁴-trimethyl-2-oxobutanediamide)-iron(III)-complex

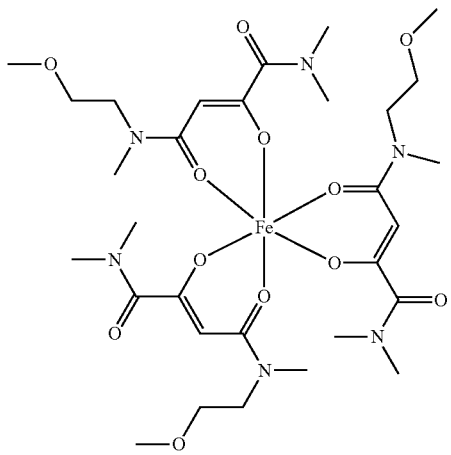

0.44 g (2.7 mmol) iron(III) chloride were dissolved in 20 ml water and 1.9 g (8.1 mmol) N⁴-(2-methoxyethyl)-N¹,N¹,N⁴-trimethyl-2-oxobutanediamide were added. Stirring was carried out for 15 minutes at room temperature, 1.47 g (10.8 mmol) sodium acetate trihydrate were added and stirred for further 20 min. The reaction mixture was extracted with 50 ml chloroform three times, dried over sodium sulfate and concentrated until dryness. The residue was stripped with 50 ml toluene two times. Drying was carried out at 50° C. for three days under fine vacuum. 1.8 g product with a purity of 80% were obtained.

IR (in substance, cm⁻¹): 3487, 2929, 1719, 1635, 1602, 1564, 1514, 1486, 1391, 1359, 1302, 1261, 1197, 1164, 1112, 1064, 1033, 1004, 964, 906, 889, 827, 807, 770, 713, 664.

Elemental analysis: C, 48.17%; H, 6.9%; N, 10.98%.

Fe content: 6.0% [m/m].

14. Tris-(N⁴-(2-methoxyethyl)-N¹,N¹-dimethyl-2-oxobutanediamide)-iron(III)-complex

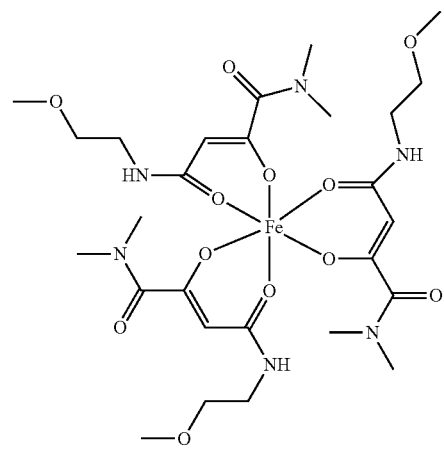

358 mg (2.20 mmol) iron(III) chloride were dissolved in 16 ml water and 1.43 g (6.61 mmol) N⁴-(2-methoxyethyl)-N¹,N¹-dimethyl-2-oxobutanediamide were added. Stirring was carried out for 15 minutes at room temperature, 1.20 g (8.82 mmol) sodium acetate trihydrate were added and stirred for further 30 min. The reaction mixture was extracted with chloroform five times, dried over sodium sulfate and concentrated until dryness. The residue was stripped with 50 ml toluene two times. Drying was carried out at 50° C. for three days under fine vacuum. 1.39 g product with a purity of 83% were obtained.

IR (in substance, cm⁻¹): 3274, 3119, 2930, 1720, 1622, 1569, 1523, 1491, 1437, 1393, 1273, 1193, 1118, 1085, 1025, 962, 861, 777, 721, 691

Elemental analysis: C, 45.27%; H, 6.5%; N, 11.64%.

Fe content: 6.6% [m/m].

15. Tris-(ethyl-N-[4-(dimethylamino)-3,4-dioxobutanoyl]-N-methylglycinate)-iron(III)-complex

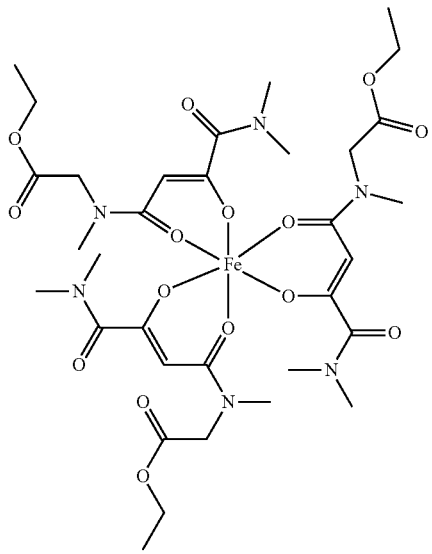

237 mg (1.46 mmol) iron(III) chloride were dissolved in 16 ml water and 1.13 g (4.38 mmol) ethyl-N-[4-(dimethylamino)-3,4-dioxobutanoyl]-N-methylglycinate were added. Stirring was carried out for 15 minutes at room temperature, 794 mg (5.84 mmol) sodium acetate trihydrate were added and stirred for further 30 min. The reaction mixture was extracted with chloroform five times, dried over sodium sulfate and concentrated until dryness. The residue was stripped with 50 ml toluene two times. Drying was carried out at 50° C. for three days under fine vacuum and 860 mg (71%) product were obtained.

IR (in substance, cm$^{-1}$): 3468, 2936, 2324, 2051, 1981, 1739, 1634, 1603, 1563, 1515, 1487, 1444, 1392, 1362, 1294, 1256, 1195, 1149, 1113, 1044, 1022, 964, 905, 861, 817, 764, 707, 667.

Elemental analysis: C, 46.67%; H, 6.1%; N, 9.80%.

Fe content: 6.6% [m/m].

16. Tris-($N^1$-(2-methoxyethyl)-$N^4$,$N^4$-dimethyl-2-oxobutanamid)-iron(III)-complex

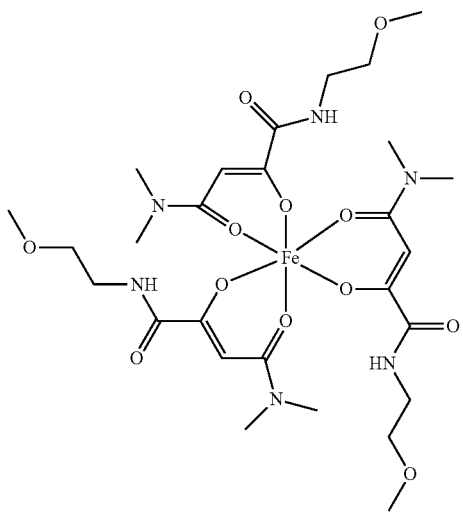

0.49 g (3.0 mmol) iron(III) chloride were dissolved in 10 ml water and 2.0 g (9.1 mmol) $N^1$-(2-methoxyethyl)-$N^4$,$N^4$-dimethyl-2-oxobutaneamide were added. Stirring was carried out for 15 minutes at room temperature followed by cooling of the reaction mixture in an ice bath. 1.66 g (12.2 mmol) sodium acetate trihydrate were added and stirred for further 15 minutes. The reaction mixture was extracted with chloroform three times, dried over sodium sulfate and concentrated until dryness. The residue was stripped with 50 ml toluene two times. Drying was carried out at 50° C. over night under fine vacuum. 1.5 g (70%) product in the form of a red solid were obtained.

IR (in substance, cm$^{-1}$): 3397, 2929, 2885, 1671, 1619, 1580, 1516, 1480, 1403, 1353, 1259, 1173, 1149, 1117, 1088, 1026, 1001, 941, 901, 881, 815, 769, 734.

Elemental analysis: C, 44.99%; H, 6.6%; N, 11.43%.

Fe content: 7.7% [m/m].

17. Tris-(ethyl-N-[4-(dimethylamino)-2,4-dioxobutanoyl]-N-methylglycinate)-iron(III)-complex

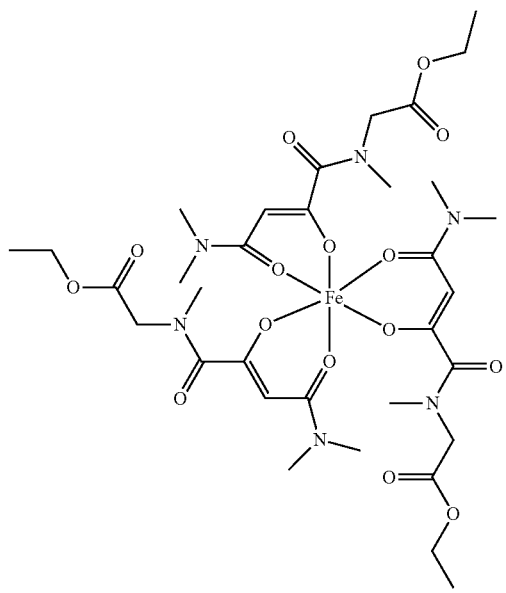

0.21 g (1.3 mmol) iron(III) chloride were dissolved in 10 ml water and 1.02 g (3.8 mmol) ethyl-N-[4-(dimethylamino)-2,4-dioxobutanoyl]-N-methylglycinate were added. Stirring was carried out for 15 minutes at room temperature followed by cooling of the reaction mixture in an ice bath. 0.71 g (5.2 mmol) sodium acetate trihydrate were added and stirred for further 15 minutes. The reaction mixture was extracted with 50 ml chloroform three times, dried over sodium sulfate and concentrated until dryness. The residue was stripped with 50 ml toluene two times. Drying was carried out at 50° C. over night under fine vacuum. 0.9 g (82%) product in the form of a red oil were obtained.

IR (in substance, cm$^{-1}$): 3485, 2981, 2936, 1738, 1641, 1601, 1571, 1508, 1477, 1444, 1397, 1357, 1297, 1258, 1199, 1176, 1105, 1027, 989, 951, 905, 865, 814, 766, 723, 662.

Elemental analysis: C, 47.10%; H, 6.7%; N, 9.11%.

Fe content: 6.6% [m/m].

18. Tris-(N$^1$-[2-(dimethylamino)-2-oxoethyl]-N$^1$,N$^4$,N$^4$-trimethyl-2-oxobutanediamide)-iron(III)-complex

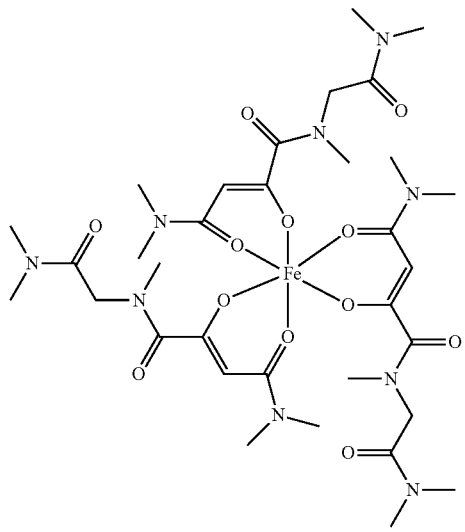

0.11 g (0.70 mmol) iron(III) chloride were dissolved in 10 ml water and 0.54 g (2.1 mmol) N$^1$-[2-(dimethylamino)-2-oxoethyl]-N$^1$,N$^4$,N$^4$-trimethyl-2-oxobutanediamide in 0.1 ml ethanol were added. Stirring was carried out for 15 minutes at room temperature and 0.38 g (2.8 mmol) sodium acetate trihydrate were added and stirred for further 15 minutes. The reaction mixture was extracted with 50 ml chloroform five times, dried over sodium sulfate and concentrated until dryness. The residue was stripped with 50 ml toluene two times. Drying was carried out at 50° C. over night under fine vacuum. 0.52 g product with a purity of 85% were obtained.

IR (in substance, cm$^{-1}$): 3455, 2934, 1779, 1630, 1572, 1508, 1479, 1398, 1357, 1303, 1259, 1178, 1152, 1106, 1060, 1027, 989, 945, 905, 823, 804, 765, 720.

Elemental analysis: C, 43.02%; H, 6.9%; N, 13.05%.
Fe content: 5.8% [m/m].

19. Tris-(ethyl-N-[4-(dimethylamino)-2,4-dioxobutanoyl]glycinate)-iron(III)-complex

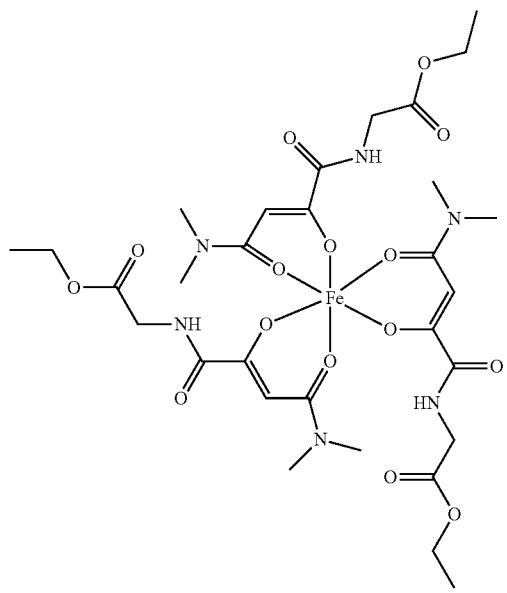

97 mg (0.60 mmol) iron(III) chloride were dissolved in 10 ml water and 459 mg (1.80 mmol) ethyl N-[4-(dimethylamino)-2,4-dioxobutanoyl]glycinate were added. Stirring was carried out for 15 minutes at room temperature followed by cooling of the reaction mixture in an ice bath. 327 mg (2.40 mmol) sodium acetate trihydrate were added and stirred for further 20 minutes. The precipitated solid was filtered off and dried at 50° C. over night under fine vacuum. 0.35 g (71%) product in the form of an orange solid was obtained.

IR (in substance, cm$^{-1}$): 3396, 3317, 2983, 2938, 2289, 2051, 1760, 1743, 1723, 1668, 1625, 1588, 1483, 1428, 1406, 1361, 1280, 1256, 1201, 1178, 1095, 1061, 1022, 994, 931, 873, 853, 822, 770, 751.

Elemental analysis: C, 44.88%; H, 5.9%; N, 10.4%.
Fe content: 6.8% [m/m].

20. Tris-(N$^1$-(2-methoxyethyl)-N$^1$,N$^4$,N$^4$-trimethyl-2-oxobutanediamide)-iron(III)-complex

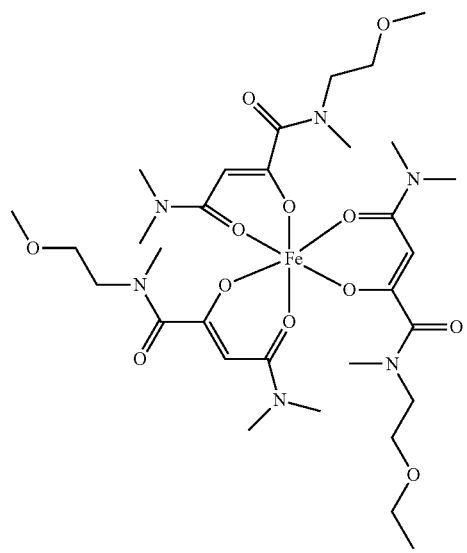

0.46 g (2.8 mmol) iron(III) chloride were dissolved in 20 ml water and 2.0 g (8.5 mmol) N$^1$-(2-methoxyethyl)-N$^1$,N$^4$,N$^4$-trimethyl-2-oxobutanediamide were added. Stirring was carried out for 15 minutes at room temperature followed by cooling of the reaction mixture in an ice bath. 1.5 g (11 mmol) sodium acetate trihydrate were added and stirred for further 20 minutes. The reaction mixture was extracted with 50 ml chloroform three times, dried over sodium sulfate and concentrated until dryness. The residue was stripped with 50 ml toluene two times. Drying was carried out at 50° C. over night under fine vacuum. 2.0 g (93%) product in the form of a red solid were obtained.

IR (in substance, cm$^{-1}$): 3492, 2929, 1633, 1605, 1568, 1510, 1479, 1449, 1427, 1398, 1354, 1287, 1260, 1200, 1175, 1108, 1067, 1006, 977, 938, 904, 892, 827, 809, 769, 712, 662.

Elemental analysis: C, 48.06%; H, 7.0%; N, 11.0%.
Fe content: 6.9% [m/m].

21. Tris-(N⁴-(2-hydroxyethyl)-N¹,N¹,N⁴-trimethyl-2-oxobutanediamide)-iron(III)-complex

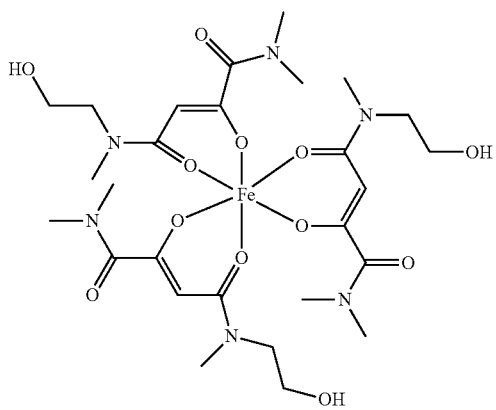

0.20 g (1.0 mmol) iron(III) acetate were suspended in 10 ml ethyl acetate and 0.65 g (3.0 mmol) N⁴-(2-hydroxyethyl)-N¹,N¹,N⁴-trimethyl-2-oxobutanediamide were added. The reaction mixture was heated up to 50° C. and 20 ml ethanol were added. Stirring was carried out for 20 minutes and the reaction mixture was concentrated until dryness. The residue was collected in an ethanol/toluene mixture (5 ml/50 ml) two times and concentrated until dryness. The residue was dried at 50° C. under fine vacuum. 0.7 g (99% yield) product in the form of red solid were obtained.

IR (in substance, cm⁻¹): 3380, 2931, 1621, 1604, 1567, 1516, 1485, 1441, 1396, 1358, 1298, 1260, 1207, 1117, 1051, 1013, 964, 940, 906, 889, 860, 805, 770, 713, 663.

Elemental analysis: C, 44.50%; H, 6.7%; N, 10.85%.

Fe content: 8.3% [m/m].

The invention claimed is:

1. A method of treatment of iron deficiency symptoms and iron deficiency anemias comprising administering to a patient at least one iron(III)-2-oxo-butanediamide complex compound comprising at least one ligand of the formula (I):

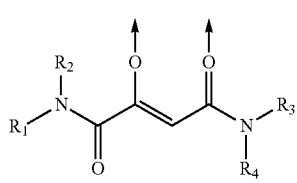

(I)

wherein
the arrows respectively represent a coordinate bond to one or different iron atoms, $R_1$ and $R_2$ are the same or different and are respectively selected from the group consisting of hydrogen, optionally substituted alkyl, and optionally substituted cycloalkyl, wherein in said alkyl groups optionally one or two carbon atoms may be replaced by oxygen,
or
$R_1$ and $R_2$, together with the nitrogen atom to which they are bonded, form an optionally substituted 3- to 6-membered ring, which may optionally contain one further heteroatom, $R_3$ and $R_4$ are the same or different and are respectively selected from the group consisting of hydrogen, optionally substituted alkyl, and optionally substituted cycloalkyl, wherein in said alkyl groups optionally one or two carbon atoms may be replaced by oxygen, or $R_3$ and $R_4$, together with the nitrogen atom to which they are bonded, form an optionally substituted 3- to 6-membered ring, which may optionally contain one further heteroatom.

2. The method of claim 1, wherein, in the at least one ligand of the formula (I):

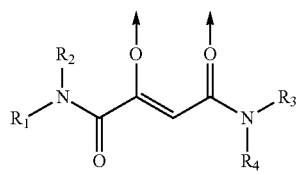

(I)

the arrows respectively represent a coordinate bond to one or different iron atoms, $R_1$ and $R_2$ are the same or different and are respectively selected from the group consisting of hydrogen, methyl, ethyl, propyl, i-propyl, n-butyl, sec-butyl and tert-butyl, and wherein said alkyl groups may be substituted with a substituent which is selected from the group consisting of alkoxy, alkoxycarbonyl, aminocarbonyl (H₂NCO—), monoalkylaminocarbonyl and dialkylaminocarbonyl, or
$R_1$ and $R_2$ together with the nitrogen atom, to which they are bonded, form an optionally substituted 5- to 6-membered ring, which may optionally contain one further heteroatom, $R_3$ and $R_4$ are the same or different and are respectively selected from the group consisting of hydrogen, optionally substituted alkyl, and optionally substituted cycloalkyl, wherein in said alkyl groups optionally one or two carbon atoms may be replaced by oxygen, or $R_3$ and $R_4$ together with the nitrogen atom, to which they are bonded, form an optionally substituted 3- to 6-membered ring, which may optionally contain one further heteroatom.

3. The method of claim 1, wherein in the at least one ligand of the formula (I):

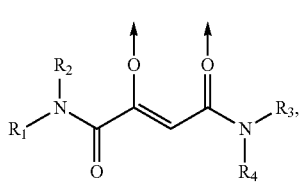

(I)

the arrows respectively represent a coordinate bond to one or different iron atoms, $R_1$ and $R_2$ are the same or different and are respectively selected from the group consisting of hydrogen, methyl, ethyl, propyl, i-propyl, n-butyl, sec-butyl and tert-butyl, and wherein said alkyl groups may be substituted with a substituent which is selected from the group consisting of alkoxy, alkoxycarbonyl, aminocarbonyl (H₂NCO—), monoalkylaminocarbonyl and dialkylaminocarbonyl, or
$R_1$ and $R_2$ together with the nitrogen atom, to which they are bonded, form pyrrolidinyl, $R_3$ and $R_4$ are the same or different and are respectively selected from the group consisting of hydrogen, alkyl, and cycloalkyl, wherein alkyl and cycloalkyl may be substituted with a substituent selected from the group consisting of: hydroxy, alkoxy, alkoxycarbonyl, aminocarbonyl (H₂NCO—), monoalkylaminocarbonyl and dialkylaminocarbonyl, $R_3$ and $R_4$ together with the nitrogen atom, to which they are bonded, form morpholinyl or pyrrolidinyl, wherein said ring groups may be substituted by hydroxy.

4. The method of claim 1, wherein in the at least one ligand of the formula (I):

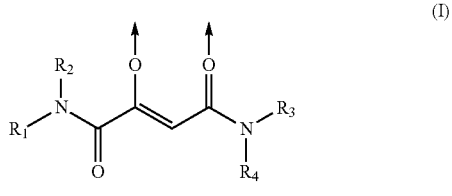

(I)

the arrows respectively represent a coordinate bond to one or different iron atoms, $R_1$ and $R_2$ are the same or different and are respectively selected from the group consisting of hydrogen, methyl, ethyl, propyl, i-propyl, n-butyl, sec-butyl and tert-butyl, $R_3$ and $R_4$ are the same or different and are respectively selected from the group consisting of hydrogen, optionally substituted alkyl, and optionally substituted cycloalkyl, wherein in said alkyl groups optionally one or two carbon atoms may be replaced by oxygen, or $R_3$ and $R_4$ together with the nitrogen atom, to which they are bonded, form an optionally substituted 3- to 6-membered ring, which may optionally contain one further heteroatom.

5. The method of claim 1, wherein in the at least one ligand of the formula (I):

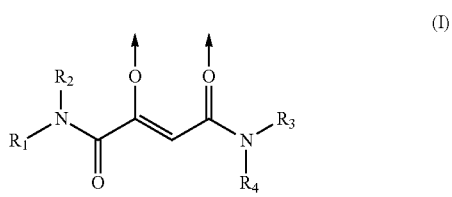

(I)

the arrows respectively represent a coordinate bond to one or different iron atoms, $R_1$ and $R_2$ are the same or different and are respectively selected from the group consisting of hydrogen and methyl,
$R_3$ and $R_4$ are the same or different and are respectively selected from the group consisting of hydrogen, optionally substituted alkyl and optionally substituted cycloalkyl, wherein in said alkyl groups optionally one or two carbon atoms may be replaced by oxygen.

6. The method of claim 1, wherein the at least one iron(III)-2-oxo-butanediamide complex compound has formula (II):

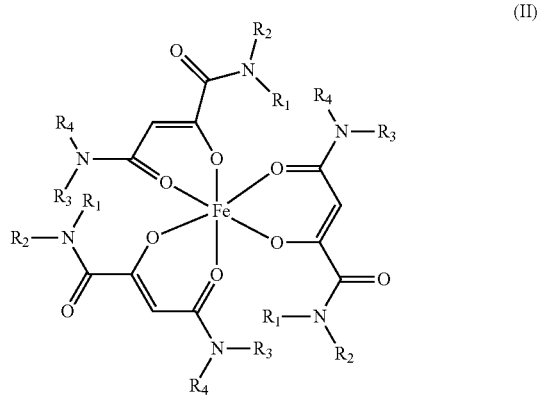

(II)

wherein $R_1$ and $R_2$ are the same or different and are respectively selected from the group consisting of hydrogen, optionally substituted alkyl, and optionally substituted cycloalkyl, wherein in said alkyl groups optionally one or two carbon atoms may be replaced by oxygen, or R1 and $R_2$, together with the nitrogen atom to which they are bonded, form an optionally substituted 3- to 6-membered ring, which may optionally contain one further heteroatom, $R_3$ and $R_4$ are the same or different and are respectively selected from the group consisting of hydrogen, optionally substituted alkyl, and optionally substituted cycloalkyl, wherein in said alkyl groups optionally one or two carbon atoms may be replaced by oxygen, or $R_3$ and $R_4$, together with the nitrogen atom to which they are bonded, form an optionally substituted 3- to 6-membered ring, which may optionally contain one further heteroatom.

7. The method of claim 6, wherein in formula (II), $R_1$ and $R_2$ each are hydrogen, and $R_3$ and $R_4$ are the same or different and are selected from the group consisting methyl and ethyl.

8. The method of claim 1, wherein the at least one iron(III)-2-oxo-butanediamide complex compound has a formula selected from the group consisting of :

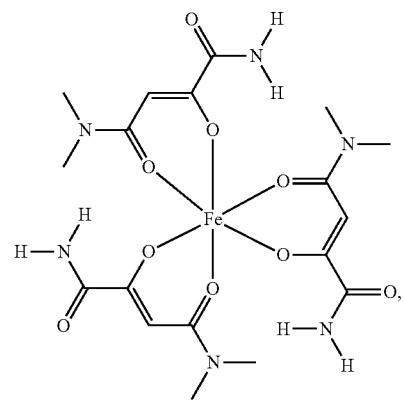

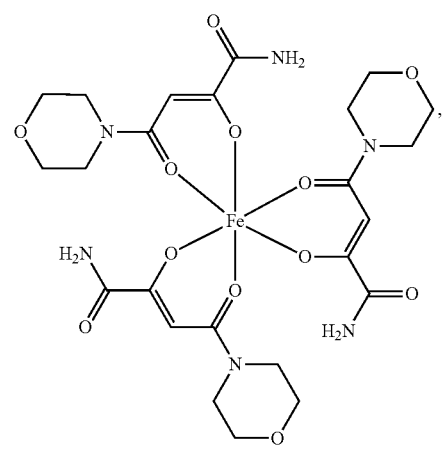

59
-continued
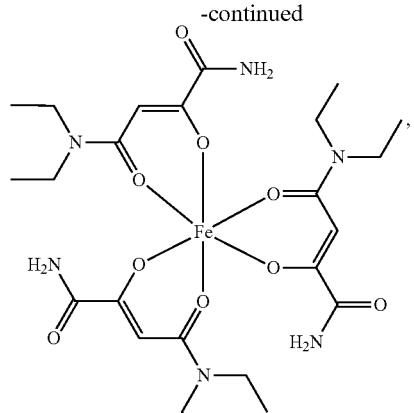
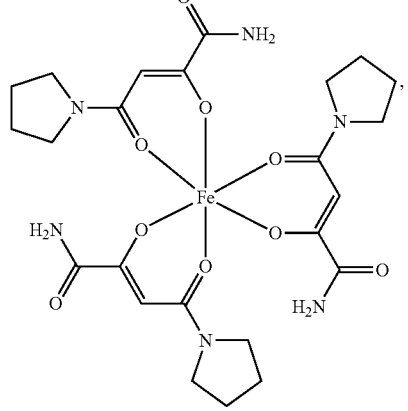
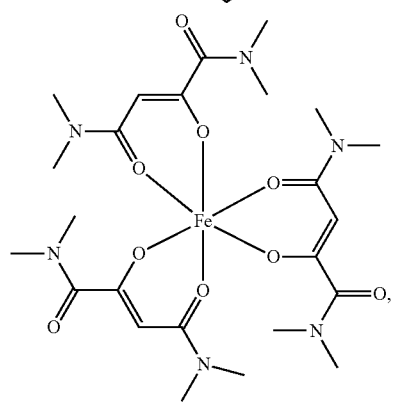
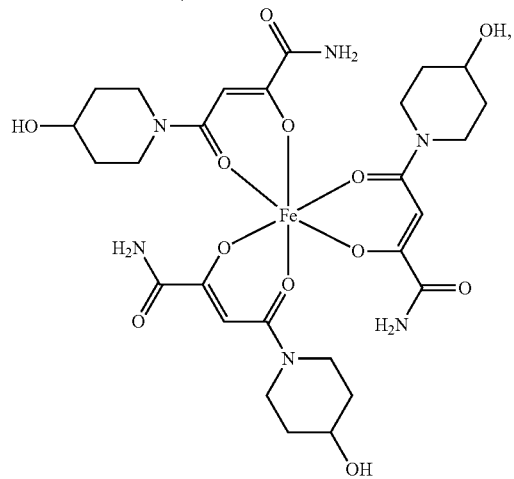
60
-continued
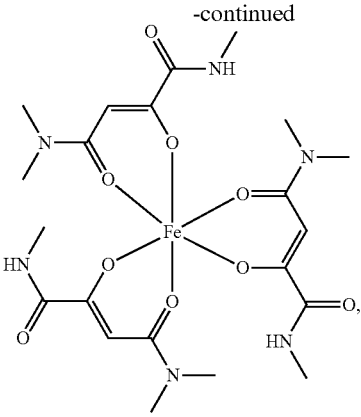
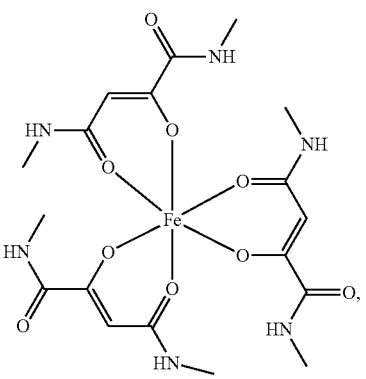
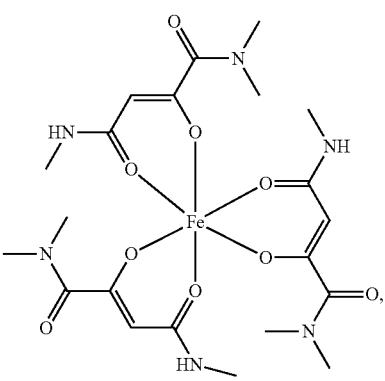
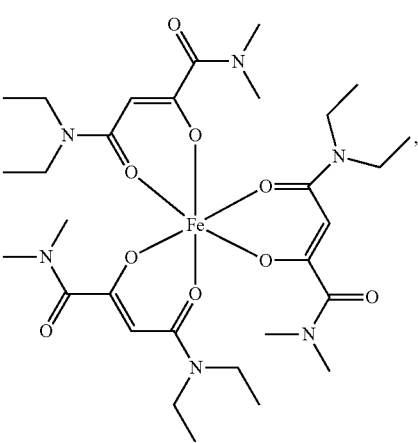

61
-continued
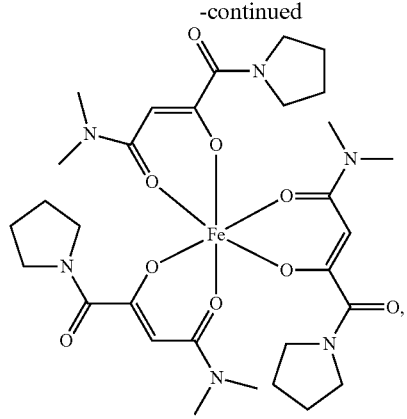
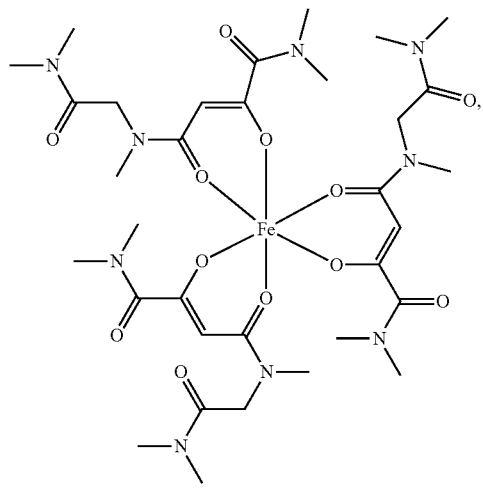
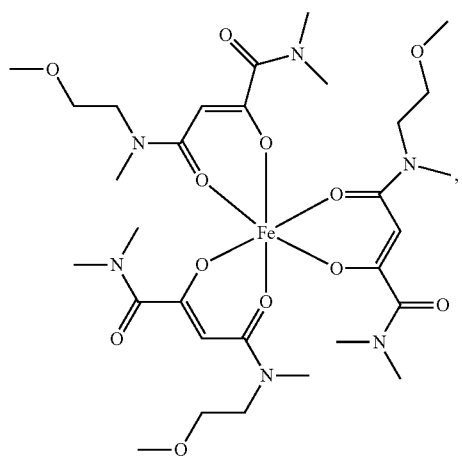
62
-continued
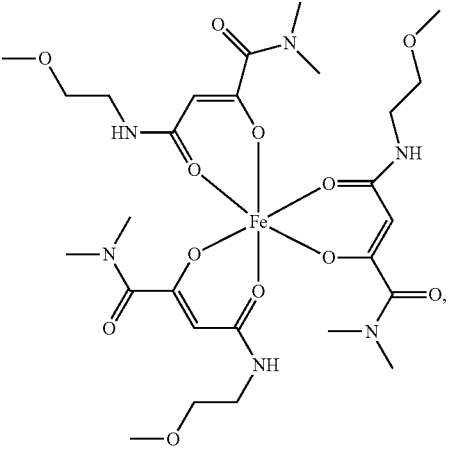
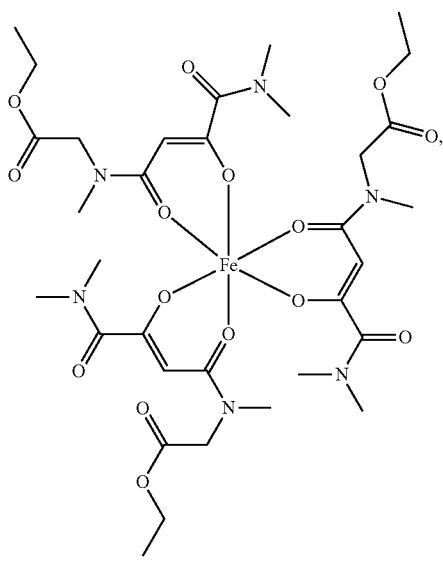
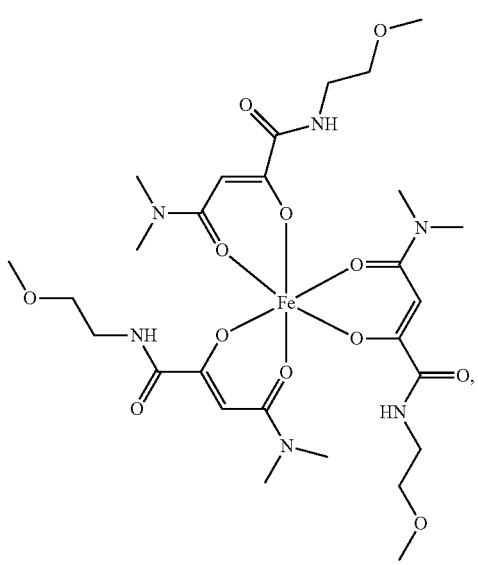

63
-continued
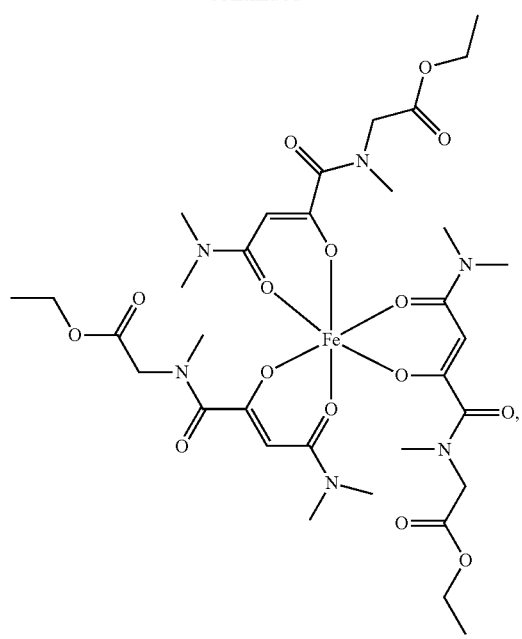
64
-continued
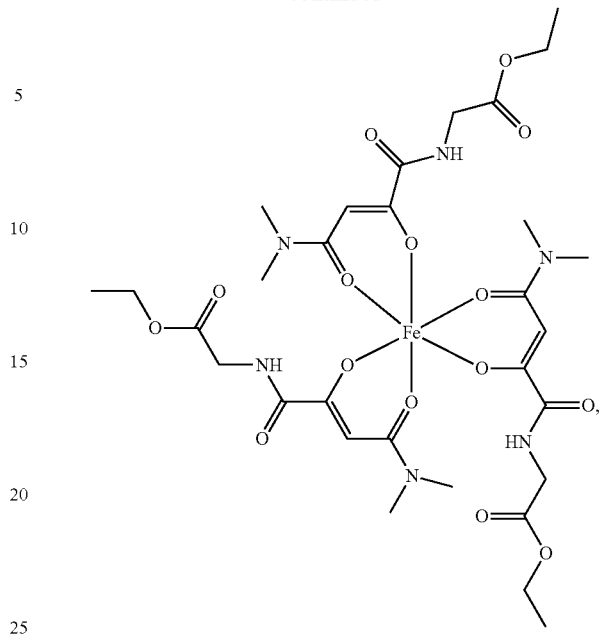
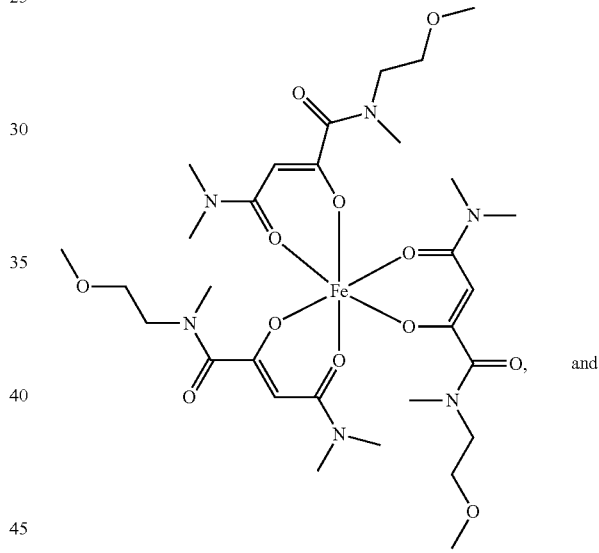
and
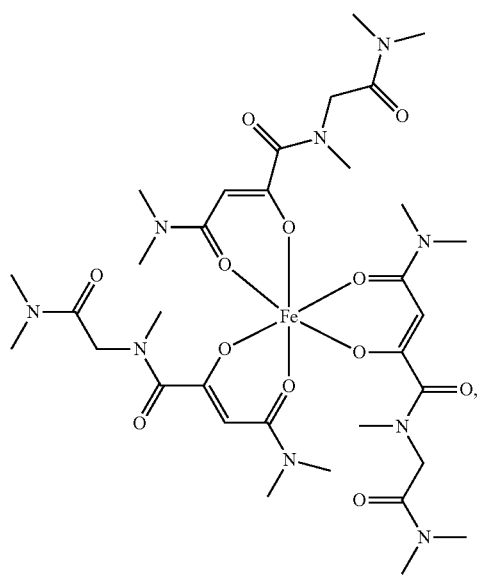
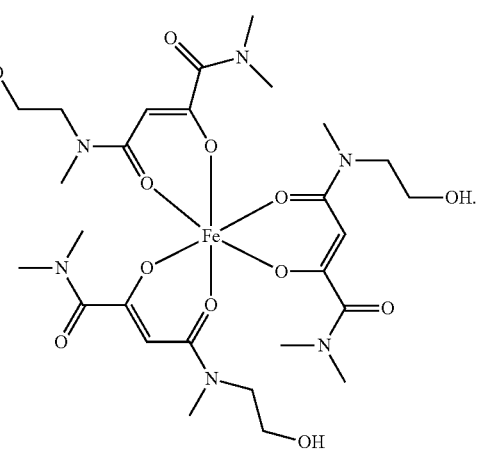

9. The method of claim 1, wherein the at least one iron(III)-2-oxo-butanediamide complex compound has a formula selected from the group consisting of:
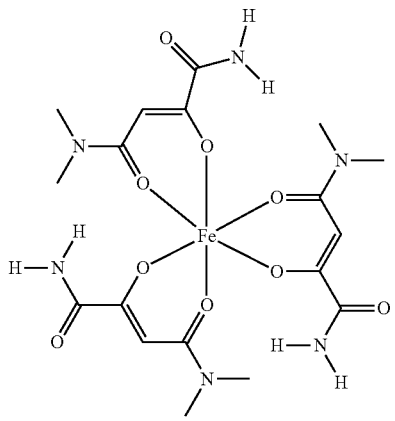
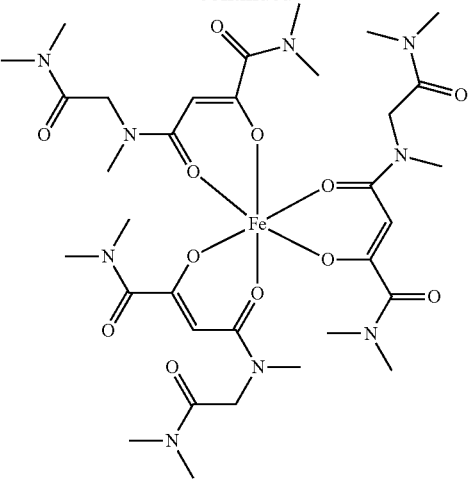
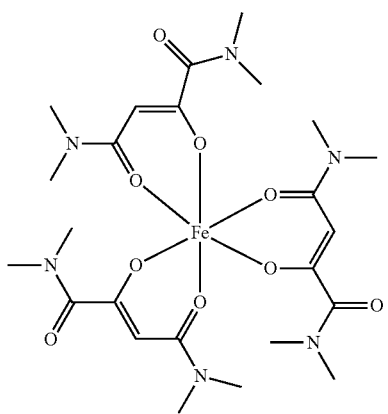
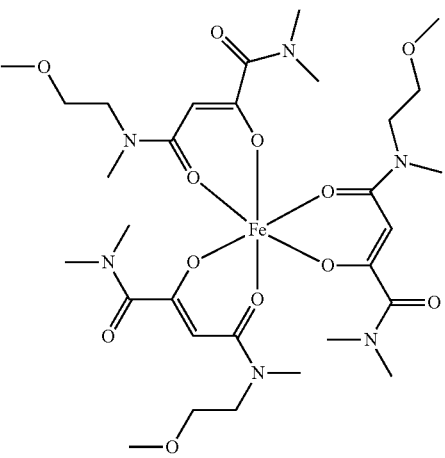
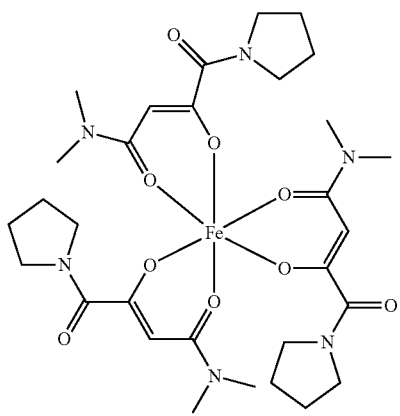
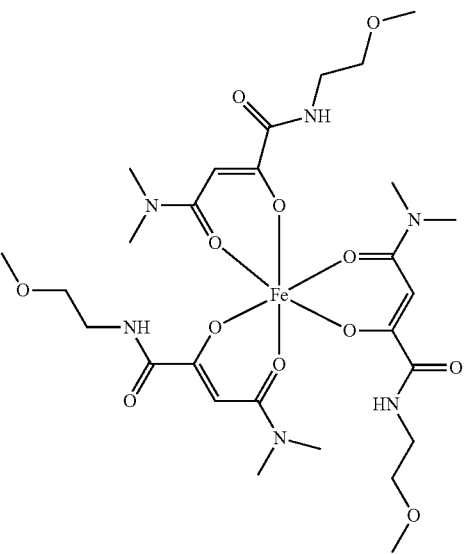

-continued
10. The method of claim 1, wherein the at least one iron(III)-2-oxo-butanediamide complex compound has a formula selected from the group consisting of:
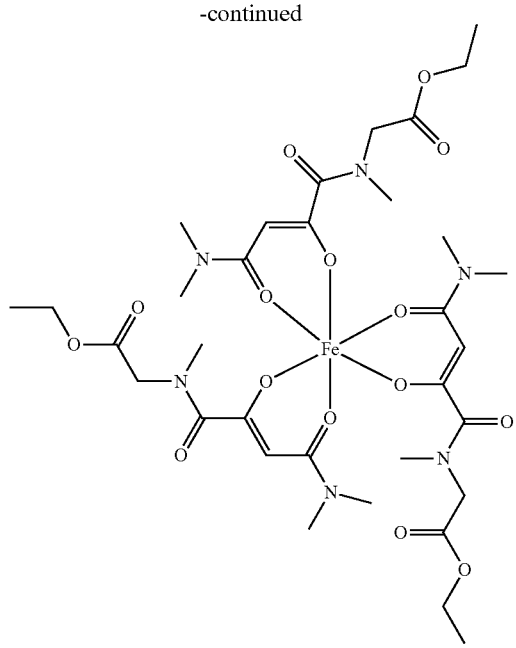
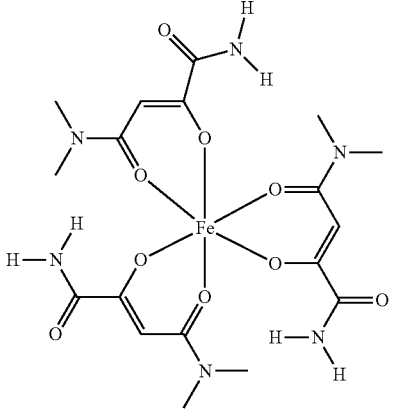
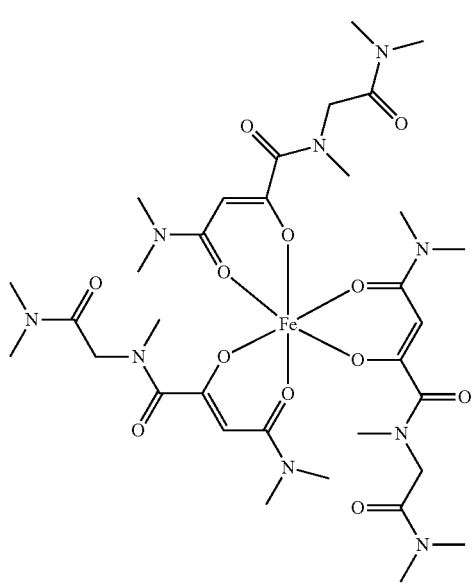
and
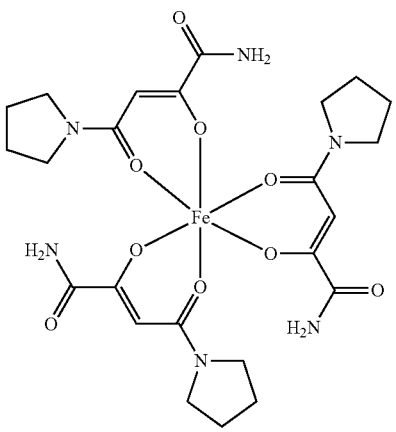
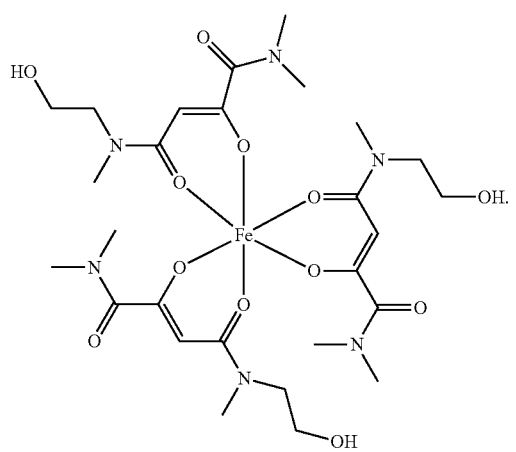

-continued

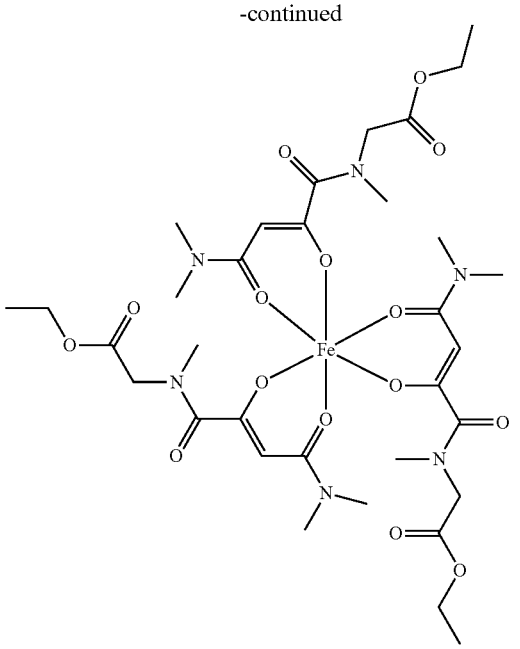

and

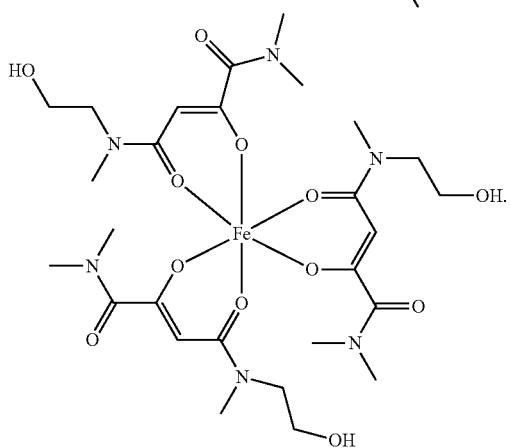

11. The method of claim 1, wherein the iron(III) complex compounds have a solubility in water at 25° C. and at pH 6.5 of at least 0.3 mg/ml based on iron.

12. The method of claim 1, wherein the symptoms of iron deficiency symptoms and iron deficiency anemias include at least one selected from the group consisting of fatigue, listlessness, lack of concentration, low cognitive efficiency, difficulties in finding the right words, forgetfulness, unnatural pallor, irritability, acceleration of heart rate, sore or swollen tongue, enlarged spleen, desire for strange foods, headaches, lack of appetite, increased susceptibility to infections, depressive moods.

13. The method of claim 1, wherein the iron deficiency symptoms or iron deficiency anemias are selected from the group consisting of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage due to ulcers, carcinoma, hemorrhoids, inflammatory disorders, as well as from taking of acetylsalicylic acid, iron deficiency anemia due to menstruation, iron deficiency anemia due to injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome caused by iron deficiency anemias, iron deficiency anemias in the case of cancer, iron deficiency anemias caused by chemotherapies, iron deficiency anemias triggered by inflammation, iron deficiency anemias in the case of congestive heart failure, iron deficiency anemias in the case of chronic kidney diseases stage 3-5, iron deficiency anemias triggered by chronic inflammation, iron deficiency anemias in the case of rheumatoid arthritis, iron deficiency anemias in the case of systemic lupus erythematosus, iron deficiency anemias in the case of inflammatory bowel diseases, iron deficiency with the hemoglobin value being in the normal range.

14. The method of claim 1, wherein the at least one iron(III)-2-oxo-butanediamide complex compound or pharmaceutically acceptable salts thereof are orally administered to the patient.

15. The method of claim 1, wherein the at least one iron(III)-2-oxo-butanediamide complex compound or pharmaceutically acceptable salts thereof are in the form of a tablet or capsule.

16. A medicament for the use in the treatment of iron deficiency symptoms and iron deficiency anemias comprising at least one iron(III)-2-oxo-butanediamide complex compound comprising at least one ligand of the formula (I):

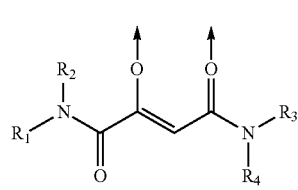

(I)

wherein
the arrows respectively represent a coordinate bond to one or different iron atoms, $R_1$ and $R_2$ are the same or different and are respectively selected from the group consisting of hydrogen, optionally substituted alkyl, and optionally substituted cycloalkyl, wherein in said alkyl groups optionally one or two carbon atoms may be replaced by oxygen,
or
$R_1$ and $R_2$, together with the nitrogen atom to which they are bonded, form an optionally substituted 3- to 6-membered ring, which may optionally contain one further heteroatom, $R_3$ and $R_4$ are the same or different and are respectively selected from the group consisting of hydrogen, optionally substituted alkyl, and optionally substituted cycloalkyl, wherein in said alkyl groups optionally one or two carbon atoms may be replaced by oxygen, or $R_3$ and $R_4$, together with the nitrogen atom to which they are bonded, form an optionally substituted 3- to 6-membered ring, which may optionally contain one further heteroatom.

17. The medicament of claim 16, further comprising at least one physiologically acceptable carrier or excipient.

18. The medicament of claim 16, further comprising at least one further medicament which acts on the iron metabolism.

* * * * *